US008673011B2

(12) United States Patent
Theofilos et al.

(10) Patent No.: US 8,673,011 B2
(45) Date of Patent: Mar. 18, 2014

(54) EXPANDABLE CAGE

(75) Inventors: Charles Theofilos, Palm Beach Gardens, FL (US); Todd Wallenstein, Ashburn, VA (US); Adam Wassinger, Reston, VA (US); Larry McClintock, Gore, VA (US); Kevin R. Strauss, Columbia, MD (US)

(73) Assignee: K2M, Inc., Leesburg, VA (US)

( * ) Notice: Subject to any disclaimer, the term of this patent is extended or adjusted under 35 U.S.C. 154(b) by 1084 days.

(21) Appl. No.: 12/602,868

(22) PCT Filed: Mar. 30, 2009

(86) PCT No.: PCT/US2009/038780
§ 371 (c)(1),
(2), (4) Date: Dec. 3, 2009

(87) PCT Pub. No.: WO2009/151734
PCT Pub. Date: Dec. 17, 2009

(65) Prior Publication Data
US 2010/0179594 A1 Jul. 15, 2010

Related U.S. Application Data

(60) Provisional application No. 61/072,176, filed on Mar. 28, 2008, provisional application No. 61/087,046, filed on Aug. 7, 2008.

(51) Int. Cl.
*A61F 2/44* (2006.01)

(52) U.S. Cl.
USPC .................. 623/17.16; 623/17.15; 623/17.11

(58) Field of Classification Search
USPC .......................................... 623/17.11, 17.16
See application file for complete search history.

(56) References Cited

U.S. PATENT DOCUMENTS 4,554,914 A 11/1985 Kapp et al.
5,236,460 A 8/1993 Barber
(Continued)

FOREIGN PATENT DOCUMENTS

SU 1560184 A1 4/1990
WO WO 2008/005627 A2 1/2008

OTHER PUBLICATIONS

ISR from Int'l Application No. PCT/US2009/038787 dated May 27, 2009.

(Continued)

*Primary Examiner* — Nicholas Woodall
*Assistant Examiner* — Christine Nelson
(74) *Attorney, Agent, or Firm* — Carter, DeLuca, Farrell & Schmidt, LLP

(57) ABSTRACT

An apparatus supports the spine between vertebrae and promotes spinal fusion. The apparatus generally includes a first supporting member, a second support member, and an expansion member. The first support member has a first longitudinal passage extending therethrough, a first supporting end configured to engage tissue, and a rack configured to engage a tool. The second supporting member contains a second longitudinal passage extending therethrough and a second supporting end configured to engage tissue. The second longitudinal passage is dimensioned to receive at least a portion of the first supporting member. The first and second supporting members are configured to move with respect to each other. The expansion member is removably positioned between the first and second supporting members and is adapted to maintain the first and second supporting members in a fixed relative position.

21 Claims, 34 Drawing Sheets

(56) References Cited

U.S. PATENT DOCUMENTS

| | | | |
|---|---|---|---|
| 5,290,312 A | 3/1994 | Kojimoto et al. |
| 5,336,223 A | 8/1994 | Rogers |
| 5,360,430 A | 11/1994 | Lin |
| 5,458,641 A | 10/1995 | Ramirez Jimenez |
| 5,571,190 A | 11/1996 | Ulrich et al. |
| 5,571,192 A | 11/1996 | Schönhöffer |
| 5,702,455 A | 12/1997 | Saggar |
| 5,723,013 A | 3/1998 | Jeanson et al. |
| 5,776,198 A | 7/1998 | Rabbe et al. |
| 5,980,522 A | 11/1999 | Koros et al. |
| 5,989,290 A | 11/1999 | Biedermann et al. |
| 6,176,881 B1 | 1/2001 | Schär et al. |
| 6,183,517 B1 | 2/2001 | Suddaby |
| 6,193,755 B1 | 2/2001 | Metz-Stavenhagen et al. |
| 6,193,756 B1 | 2/2001 | Studer et al. |
| 6,200,348 B1 | 3/2001 | Biedermann et al. |
| 6,241,769 B1 | 6/2001 | Nicholson et al. |
| 6,296,665 B1 | 10/2001 | Strnad et al. |
| 6,332,895 B1 | 12/2001 | Suddaby |
| 6,375,683 B1 | 4/2002 | Crozet et al. |
| 6,395,034 B1 | 5/2002 | Suddaby |
| 6,419,705 B1 | 7/2002 | Erickson |
| 6,500,178 B2 | 12/2002 | Zucherman et al. |
| 6,524,341 B2 | 2/2003 | Läng et al. |
| 6,562,074 B2 | 5/2003 | Gerbec et al. |
| 6,610,090 B1 | 8/2003 | Böhm et al. |
| 6,616,695 B1 | 9/2003 | Crozet et al. |
| 6,648,917 B2 | 11/2003 | Gerbec et al. |
| 6,660,038 B2 | 12/2003 | Boyer, II et al. |
| 6,730,088 B2 | 5/2004 | Yeh |
| 6,752,832 B2 | 6/2004 | Neumann |
| 6,770,096 B2 | 8/2004 | Bolger et al. |
| 6,830,589 B2 | 12/2004 | Erickson |
| 6,852,129 B2 | 2/2005 | Gerbec et al. |
| 6,863,673 B2 | 3/2005 | Gerbec et al. |
| 6,866,682 B1 | 3/2005 | An et al. |
| 6,908,485 B2 | 6/2005 | Crozet et al. |
| 7,025,787 B2 | 4/2006 | Bryan et al. |
| 7,056,343 B2 | 6/2006 | Schäfer et al. |
| 7,094,257 B2 | 8/2006 | Mujwid et al. |
| 7,156,874 B2 | 1/2007 | Paponneau et al. |
| 7,285,134 B2 | 10/2007 | Berry et al. |
| 2003/0130739 A1 | 7/2003 | Gerbec et al. |
| 2003/0181980 A1 | 9/2003 | Berry et al. |
| 2004/0186569 A1 | 9/2004 | Berry |
| 2005/0060034 A1 | 3/2005 | Berry et al. |
| 2005/0209697 A1 | 9/2005 | Paponneau et al. |
| 2006/0100710 A1 | 5/2006 | Gutlin et al. |
| 2006/0129244 A1 | 6/2006 | Ensign |
| 2006/0200244 A1 | 9/2006 | Assaker |
| 2006/0241762 A1 | 10/2006 | Kraus |
| 2007/0010887 A1 | 1/2007 | Williams et al. |
| 2007/0032871 A1 | 2/2007 | Michelson |
| 2007/0100340 A1 | 5/2007 | Lange et al. |
| 2007/0250171 A1 | 10/2007 | Bonin, Jr. |
| 2007/0255408 A1* | 11/2007 | Castleman et al. ........ 623/17.11 |
| 2007/0270968 A1 | 11/2007 | Baynham et al. |
| 2007/0282441 A1 | 12/2007 | Stream et al. |

OTHER PUBLICATIONS

ISR from Int'l Application No. PCT/US2009/038780 dated Nov. 13, 2009.

* cited by examiner

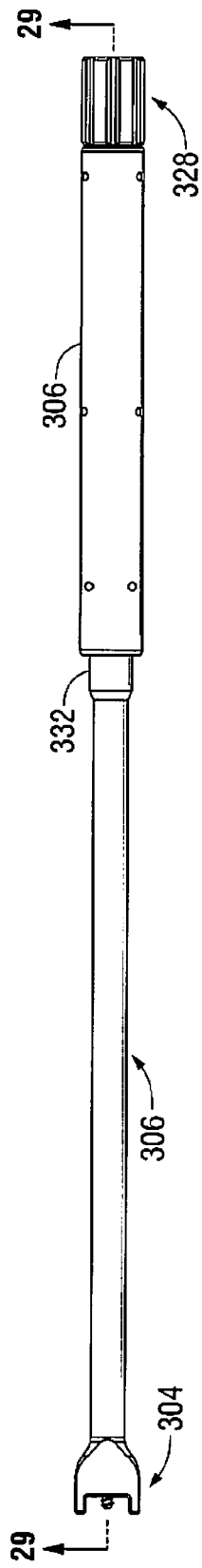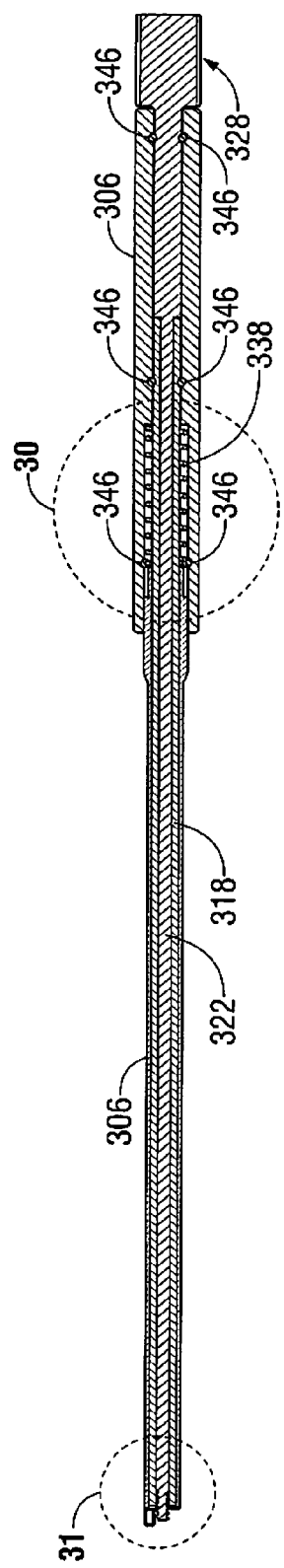
FIG. 28
FIG. 29

EXPANDABLE CAGE

CROSS-REFERENCE TO RELATED APPLICATIONS

The present application claims priority to, and the benefit of, U.S. Provisional Patent Application No. 61/072,176, filed on Mar. 28, 2008, and U.S. Provisional Patent Application No. 61/087,046, filed on Aug. 7, 2008, the contents of each of these prior applications are incorporated by reference herein in their entirety.

BACKGROUND

1. Technical Field

The present disclosure relates to apparatus and methods for treating spinal conditions and, more particularly, for supporting adjacent vertebrae.

2. Background of Related Art

The human spine includes thirty-three vertebrae. The vertebrae interlock with one another to form a spinal column. Each vertebra has a cylindrical bony body (vertebral body), two pedicles extending from the vertebral body, a lamina extending from the pedicles, two wing-like projections extending from the pedicles, a spinous process extending from the lamina, a pars interarticularis, two superior facets extending from the pedicles, and two inferior facets extending from the lamina. The vertebrae are separated and cushioned by thin pads of tough, resilient fiber known as inter-vertebral discs. Inter-vertebral discs provide flexibility to the spine and act as shock absorbers during activity. A small opening (foramen) located between each vertebra allows passage of nerves. When the vertebrae are properly aligned, the nerves pass through without a problem. However, when the vertebrae are misaligned or a constriction is formed in the spinal canal, the nerves get compressed and may cause back pain, leg pain, or other neurological disorders.

Disorders of the spine that may cause misalignment of the vertebrae or constriction of the spinal canal include spinal injuries, infections, tumor formation, herniation of the inter-vertebral discs (i.e., slippage or protrusion), arthritic disorders, and scoliosis. In these pathologic circumstances, surgery may be tried to either decompress the neural elements and/or fuse adjacent vertebral segments. Decompression may involve laminectomy, discectomy, or corpectomy. Laminectomy involves the removal of part of the lamina, i.e., the bony roof of the spinal canal. Discectomy involves removal of the inter-vertebral discs. Corpectomy involves removal of the vertebral body as well as the adjacent inter-vertebral discs.

A number of spinal surgical devices may be used to promote bony fusion after decompressing the spinal nerves. For instance, surgeons often replace the diseased vertebral tissue with one or more spinal cages and bone support matrix. Spinal cages support adjacent vertebral segments, while furthering spinal fusion of adjacent vertebral bodies. Scientists and clinicians have developed a number of devices and methods for decompressing spinal nerves. Improvements to this methods and devices are nevertheless still possible.

SUMMARY

The present disclosure relates to an apparatus for supporting adjacent vertebrae and promoting spinal fusion. The apparatus generally includes a first supporting member, a second support member, and an expansion member. The first support member has a first longitudinal passage extending therethrough, a first supporting end configured to engage tissue, and a rack configured to engage a tool. The second supporting member contains a second longitudinal passage extending therethrough and a second supporting end configured to engage tissue. The second longitudinal passage is dimensioned to receive at least a portion of the first supporting member. The first and second supporting members are configured to move with respect to each other. The expansion member is removably positioned between the first and second supporting members and is adapted to maintain the first and second supporting members in a fixed relative position.

In addition to the apparatus, the present disclosure relates to a method for supporting adjacent vertebrae. This method includes the following steps: (1) providing an apparatus including first and second supporting members configured to move relative to each other and an expansion member removably positioned between the first and second supporting members, the first supporting member including a rack disposed along an inner surface thereof, wherein the second supporting member defines a longitudinal passage adapted to receive at least a portion of the first supporting member; (2) providing a driver configured to engage the rack of the first supporting member; wherein first and second supporting members are adapted to move relative to each other upon rotation of the driver when the driver is operably engaged with the rack; (3) removing vertebral tissue; (4) inserting the apparatus between adjacent vertebrae; (5) engaging the driver with the rack; (6) actuating the driver with the driver in engagement with the rack to adjust a relative position of the first and second supporting members; and (7) positioning the expansion member between the first and second supporting members to maintain the relative position of the first and second supporting members; and (8) disengaging and removing the driver.

The present disclosure further relates to a tool for inserting an expandable cage inside a body. This tool includes an insertion portion adapted to position an expandable cage inside a body, a driver for adjusting a height of the expandable cage, and a holding portion configured to hold the expandable cage. The holding portion interconnects the insertion portion and the driver. The driver is rotatably mounted on the holding portion.

In addition, the present disclosure relates to a tool assembly for inserting an expandable cage inside a body. This tool assembly includes a handle, an elongate section extending from the handle, a holding section operatively coupled to the elongate section, a rod extending through the elongate section and the holding section, and a bar partially disposed within the holding section. The rod includes a threaded tip positioned at a distal portion thereof. The threaded tip protrudes distally from the holding section and is configured to rotate relative to the elongate section. The bar includes a head having a plurality of teeth and is configured to rotate relative to the holding section.

BRIEF DESCRIPTION OF THE FIGURES

FIG. 28 is a top view of the driver of FIG. 24;

FIG. 29 is a cross-sectional view of the driver of FIG. 24; taken along section line 29-29 of FIG. 28;

DETAILED DESCRIPTION OF THE EMBODIMENTS

Figure 1:
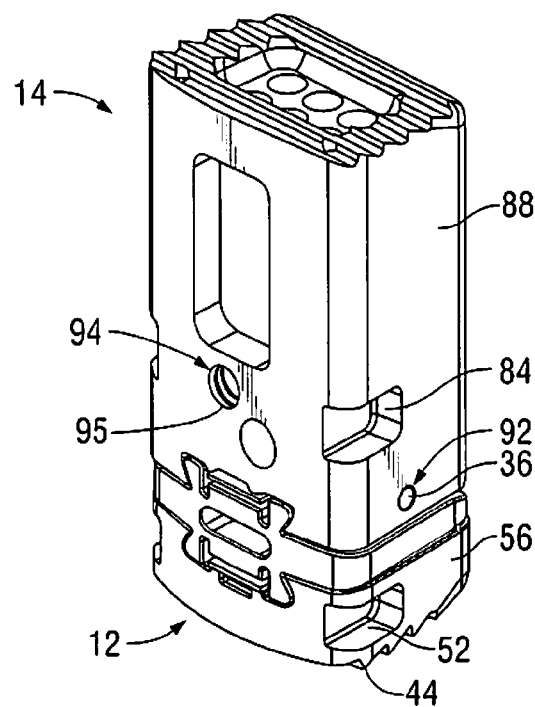
FIG. 1 is a perspective view of an expandable cage according to an embodiment of the present disclosure with an expansion member secured between the first and second supporting members.

Embodiments of the presently disclosed devices and methods will now be described in detail with reference to the drawings, wherein like reference numerals identify similar or identical elements. In the drawings and in the description that follows, the term "proximal" will refer to the end of a tool or device that is closest to the operator, while the term "distal" will refer to the end of the tool or device that is farthest from the operator. In addition, the term "cephalad" is used in this application to indicate a direction toward a patient's head, whereas the term "caudad" indicates a direction toward the patient's feet. Further still, for the purposes of this application, the term "medial" indicates a direction toward the middle of the body of the patient, whilst the term "lateral" indicates a direction toward a side of the body of the patient (i.e., away from the middle of the body of the patient). The term "posterior" indicates a direction toward the patient's back, and the term "anterior" indicates a direction toward the patient's front. As used herein, a "bone support matrix" is a material that facilitates new bone growth between the opposing vertebral bodies. Suitable bone support matrices can be resorbable or nonresorbable and osteoconductive or osteoinductive. Examples of suitable bone support matrices include synthetic materials, bone morphogenic proteins (BMPs), and heterologous, homologous, or autologous bone and derivatives thereof. The bone support matrix may be radiolucent on x-rays.

Figure 2:
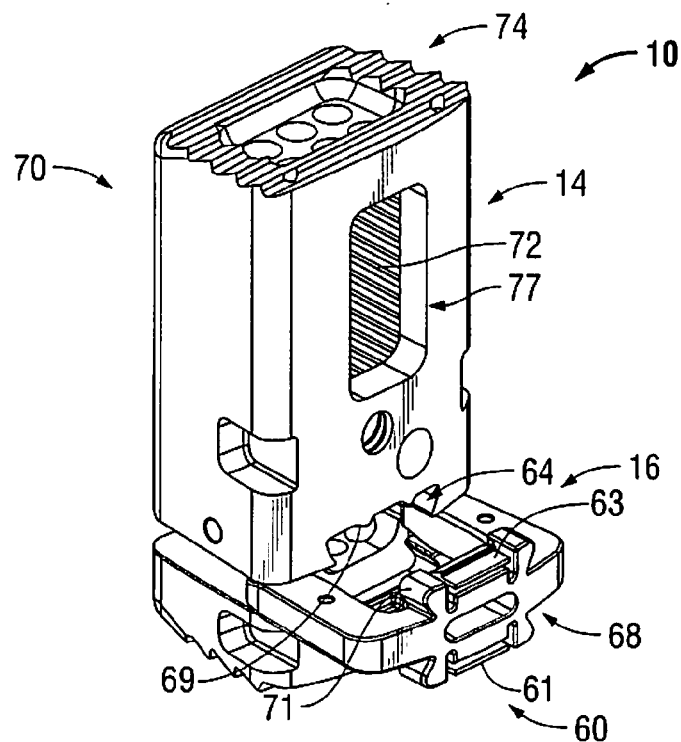
FIG. 2 is a perspective view of the expandable cage of FIG. 1 with the expansion member partially removed from its secured position between the first and second supporting members.

FIGS. 1 and 2 show an expandable cage 10 designed for supporting adjacent vertebra and promoting spinal fusion. Expandable cage 10, which may be made of autologous bone graft, bone allograft, polyetheretherketone (PEEK), titanium, stainless steel, cobalt chrome, polymeric materials, a combination thereof, or any other suitable material, includes first and second supporting members 12, 14 configured to move relative to each other and an expansion member 16 removably positioned between first and second supporting members 12, 14. Expandable cage 10 may be part of a kit including first and second supporting members 12, 14 and several expansion members 16 of different sizes. The different expansion members 16 are dimensioned to maintain first and second supporting members 12, 14 in different relative positions. The plurality of expansion members 16 allows a user to adjust and fix expandable cage 10 at different heights. During operation, the user can adjust the relative position of first and second supporting members 12, 14 to accommodate expandable cage 10 in a variable space located between adjacent vertebrae. After placing expandable cage 10 in such space, the user positions the appropriate expansion member 16 between first and second supporting members 12, 14 to maintain their relative position, thus fixing the expandable cage 10 at the desired height.

Figure 3:
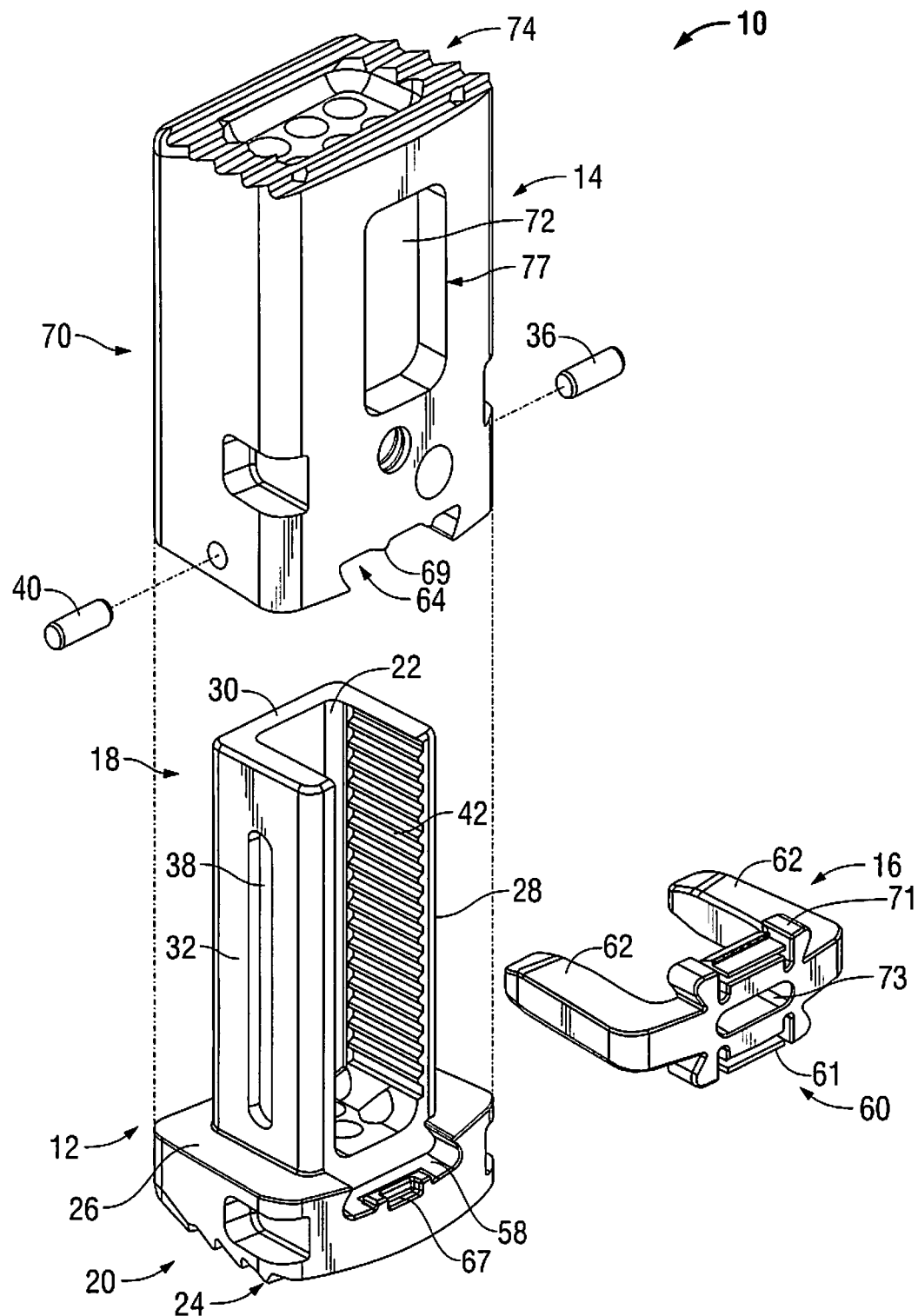
FIG. 3 is perspective exploded view of the expandable cage of FIG. 1.
Figure 9:
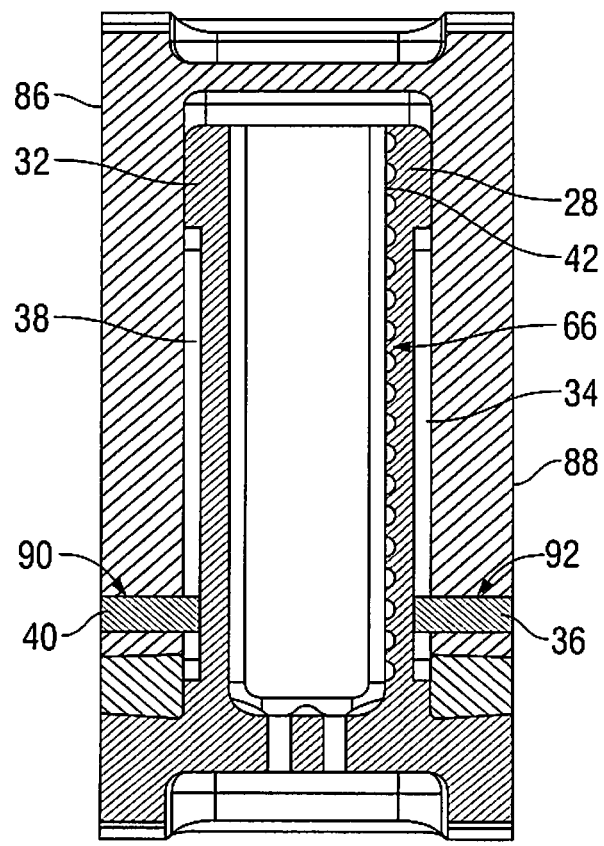
FIG. 9 is a cross-sectional view of the expandable cage of FIG. 1, taken along section line 9-9 of FIG. 4.

With reference to FIGS. 3 and 9, first supporting member 12 of expandable cage 10 includes a first supporting end 20 and an elongate body 18 extending from first supporting end 20. As seen in FIG. 3, elongate body 18 may be a C-shaped structure. It is envisioned, however, that elongate body 18 may have any suitable structure, shape or configuration. Regardless of its shape, elongate body 18 defines a longitudinal passage 22 extending therethrough. Longitudinal passage 22 is adapted to receive optional autologous bone graft, bone allograft, bone slurry, bone chips, bone morphogenic protein or any other bone support matrix suitable for promoting bony union between vertebrae. In the embodiment depicted in FIG. 3, first, second, and third walls 28, 30, 32 collectively define longitudinal passage 22 and form elongate body 18. Each of first, second and third walls 28, 30, 32 have flat outer surfaces. Second wall 30 interconnects first and third walls 28, 32. First wall 28 is transversely secured to second wall 30, while second wall 30 is transversely attached to third wall 32. First and third walls 28, 32 are arranged in parallel with respect to each other. Second wall 30, on the other hand, is arranged in a substantially orthogonal relationship with first and third walls 28, 32.

Figure 12:
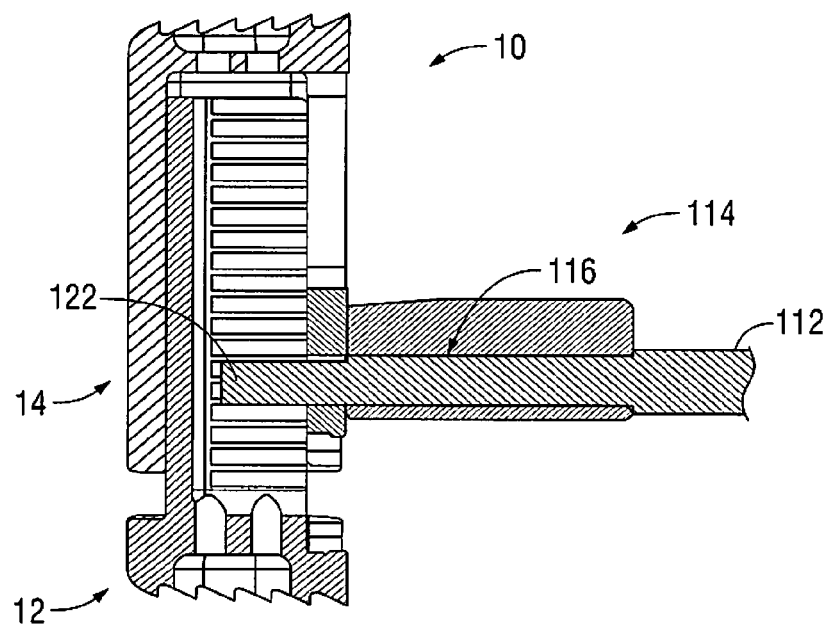
FIG. 12 is a cross-sectional view of the insertion tool of FIG. 10 holding the expandable cage of FIG. 1 without the expansion member, taken along section line 12-12 of FIG. 11.

First wall 28 contains a slot 34 disposed along an outer surface thereof, as depicted in FIG. 9. Slot 34 is configured to slidably receive a pin 36. Slot 34 and pin 36 jointly allow first and second supporting members 12, 14 to slide relative to each other while maintaining alignment of the parts, inhibiting relative rotational movement of the parts, and inhibiting separation of the parts. In addition to slot 34, first wall 28 includes a plurality of undulations or indentations 42 spreading along an inner surface thereof. Undulations 42 together form rack 66 configured to engage a head 122 of an insertion tool 100. (See for example FIGS. 12 and 14). Third wall 32 features a slot 38 formed along an outer surface thereof. Slot 38 is adapted to slidably receive a pin 40. Slot 38 and pin 48 cooperatively allow first and second support members 12, 14 to slide with respect to each other while maintaining alignment of the parts, inhibiting relative rotational movement of the parts, and inhibiting separation of the parts.

Figure 4:
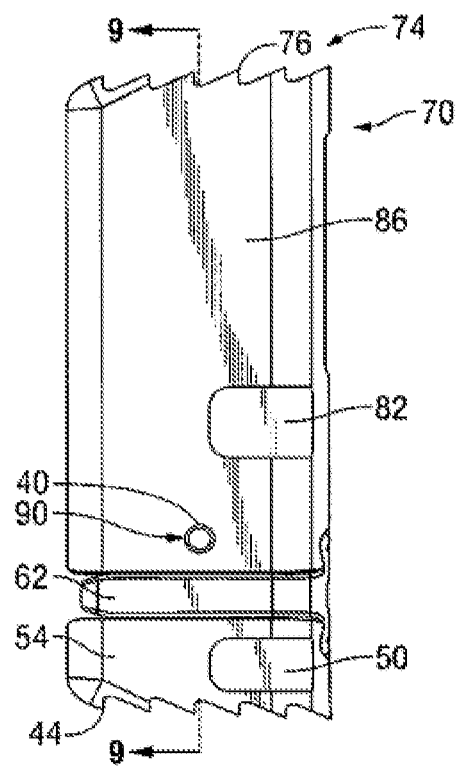
FIG. 4 is a right side view of the expandable cage of FIG. 1, showing section line 9-9.
Figure 8:
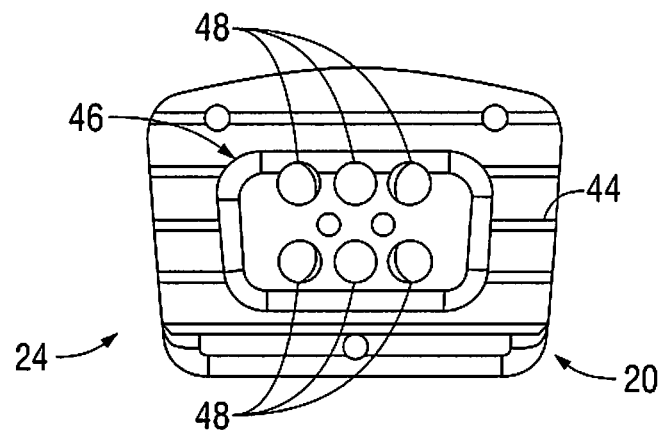
FIG. 8 is a bottom view of the expandable cage of FIG. 1.

With reference to FIGS. 3 and 8, first supporting end 20 includes an engagement surface 24 and an abutting surface 26 disposed in directly opposite relation with respect to each other. Abutting surface 26 faces second supporting member 14, whereas engagement surface 24 faces away from second supporting member 14, when second support member 14 is at least partially placed over first supporting member 12. Engagement surface 24 contains a plurality of teeth 44 adapted to engage a vertebra, or any other kind of tissue, and a recess 46 disposed around a central area thereof. Teeth 44 are arranged in longitudinal rows spreading along the width of engagement surface 24. Each tooth 44 defines an oblique angle in relation to the abutting surface 26, as seen in FIG. 4. Nonetheless, engagement surface 24 may alternatively have teeth 44 having other configurations and arrangements or any other structure capable of engaging tissue. Recess 46 has a substantially rectangular shape and is configured to receive any suitable bone support matrix to promote spinal fusion between adjacent vertebrae.

As seen in FIG. 8, first supporting member end 20 further includes at least one hole 48 disposed in recess 46. Hole 48 extends through first supporting end 20 and provides access to longitudinal passage 22 (FIG. 3). During use, bone support matrix enters longitudinal passage 22 (see FIG. 3) through hole 48. In the embodiment depicted in FIG. 8, first supporting end 20 includes six (6) holes 48 having circular cross-sections and arranged in longitudinal rows. First supporting end 20, however, may have fewer or more holes 48. Furthermore, holes 48 may have any other suitable configuration or arrangement.

Figure 13:
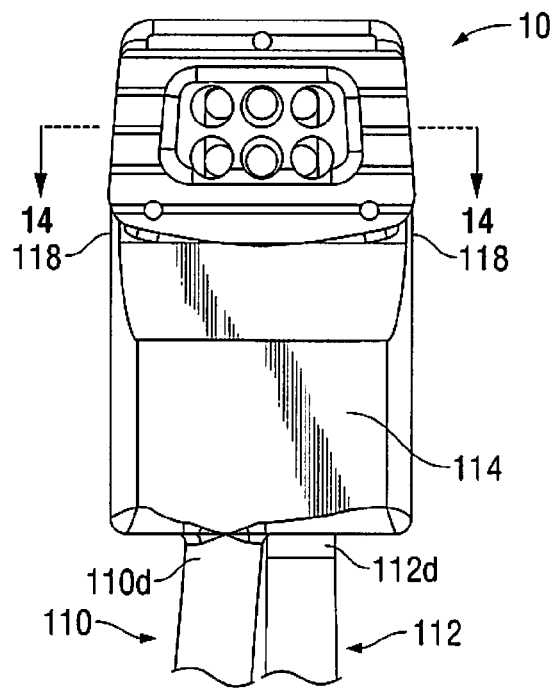
FIG. 13 is a top view of a distal portion of the insertion tool of FIG. 10 holding the expandable cage of FIG. 1 without the expansion member.

As shown in FIGS. 1 and 4, first supporting end 20 additionally includes cavities 50, 52 disposed on opposite lateral sides 54, 56 thereof. Each cavity 50, 52 (FIGS. 1 and 4) is adapted to receive arms 118 of an insertion tool 100. (See FIGS. 10 and 13). During operation, a user may advance expandable cage 10 toward the desired surgical site by positioning arms 118 of an insertion tool 100 (See FIG. 10) within cavities 50, 52 of first supporting end 20 and advancing insertion tool 100 toward the surgical site.

Referring again to FIG. 3, first supporting end 20 includes an abutment surface 26, as discussed above. Abutment surface 26 interconnects first, second, and third walls 28, 30, 32 and abuts at least a portion of expansion member 16 when expansion member 16 is placed between first and second supporting members 12, 14. To facilitate a secure connection between first and second supporting members 12, 14, abutment surface 26 includes a locking recess 58 adapted to securely receive a locking portion 60 of a backspan 59 of expansion member 16. Locking portion 60 defines an opening 73 for allowing access of bone support matrix into longitudinal passage 22. Aside from locking portion 60, expansion member 16 includes a pair of legs 62 extending transversely with respect to backspan 59 which includes locking portion 60. Locking portion 60 is configured to securely engage locking recess 58 of first supporting member 12 and a locking recess 64 formed on second supporting member 14. Altogether, locking portion 60 and locking recesses 58, 64 form a dovetail joint with a locking mechanism 68. Locking mechanism 68 may be, for example, a snap-fit coupling; however, locking mechanism 68 may include any other suitable coupling configured to connect expansion member 16 to first and second supporting members 12, 14.

Figure 5:
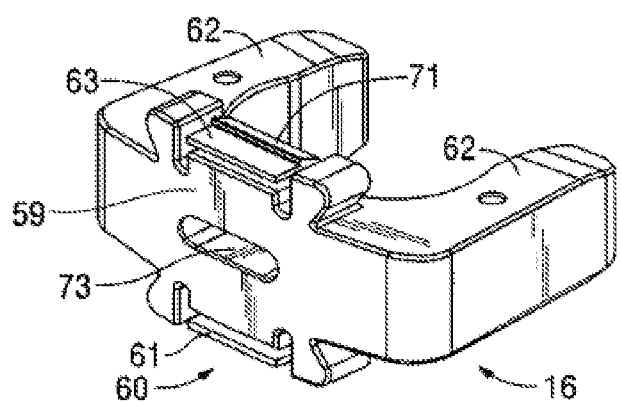
FIG. 5 is a perspective view of the expansion member of the expandable cage of FIG. 1.

As seen in FIGS. 2, 3 and 5, in one embodiment, locking portion 60 of backspan 59 includes first and second snap-fit arms 61, 63. First and second snap-fit arms 61, 63 are disposed on directly opposite surfaces of the backspan 59 relative to each other. Each of the first and second snap-fit arm 61, 63 are pivotally (or hingedly) connected to locking portion 60 at one end, i.e., cantilevered. First snap-fit arm 61 is adapted to be releasably coupled to locking recess 58 of first supporting end 20, and second snap-fit arm 63 is configured to be releasably connected to locking recess 64 of second supporting member 14. To this end, second snap-fit arm 63 includes a snap-fit detent 71. The first snap-fit arm 61 also includes a snap-fit detent (not shown). The snap-fit detent of snap-fit arm 61 is substantially identical to snap-fit detent 71 of snap-fit arm 63. Locking recesses 58, 64 each include an engagement wall 67, 69 (FIGS. 2 and 3). Each engagement wall 67, 69 is configured to engage first and second snap-fit detents 63, 71 to secure expansion member 16 to first and second supporting members 12, 14. To release expansion member 16 from first and second supporting members 12, 14, a user pivots first and second snap-fit arms 61, 63 about the cantilevered end away from engagement walls 67, 69 in order to disengage snap-fit detents 65, 71 from engagement walls 67, 69.

Figure 6:
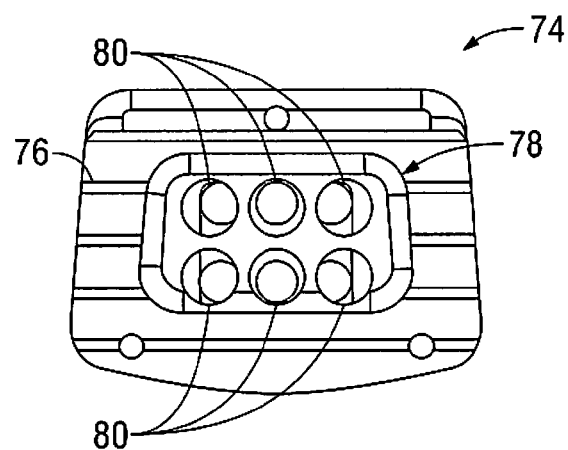
FIG. 6 is a top view of the expandable cage of FIG. 1.

With continued reference to FIG. 3, second supporting member 14 includes an elongate body 70 defining a longitudinal passage 72 and a second supporting end 74. Elongate body 70 additionally includes a rectangular aperture 77 leading to longitudinal passage 72. Longitudinal passage 72 is dimensioned to slidably receive elongate body 18 of first supporting member 12 and is configured to receive bone support matrix. Second supporting end 74 includes a plurality of teeth 76 (FIG. 6) configured to engage tissue. As seen in FIG. 6, teeth 76 are arranged in longitudinal rows spanning the width of second supporting end 74. Each tooth 76 defines an oblique angle relative to the second supporting end 74, as shown in FIG. 4. Second supporting end 74 further includes a recess 78 (FIG. 6) disposed around a central area thereof. Recess 78 is adapted to receive bone support matrix therein. Additionally, second supporting end 74 includes at least one hole 80 (FIG. 6) located in recess 78. Hole 80 provides access to longitudinal passage 72. In use, bone support matrix migrates from recess 78 to longitudinal passage 72 through hole 80. In the depicted embodiment, second supporting end 74 contains six (6) holes 80 having circular cross-sections and arranged in longitudinal rows (FIG. 6). Second supporting end 74, however, may include more or fewer holes 80 having different configurations and arrangements.

Figure 7:
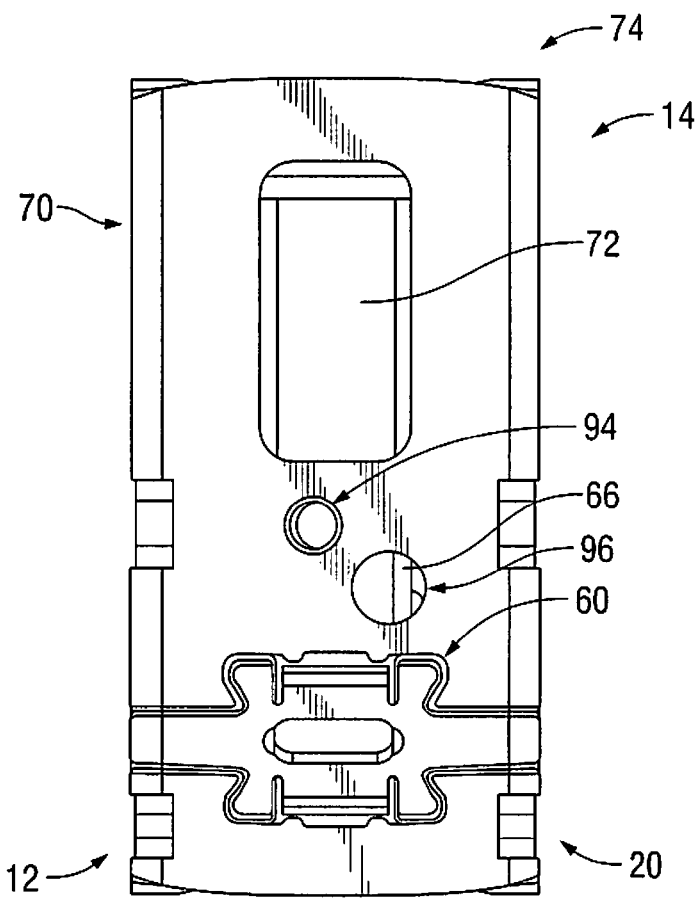
FIG. 7 is a front view of the expandable cage of FIG. 1.
Figure 37:
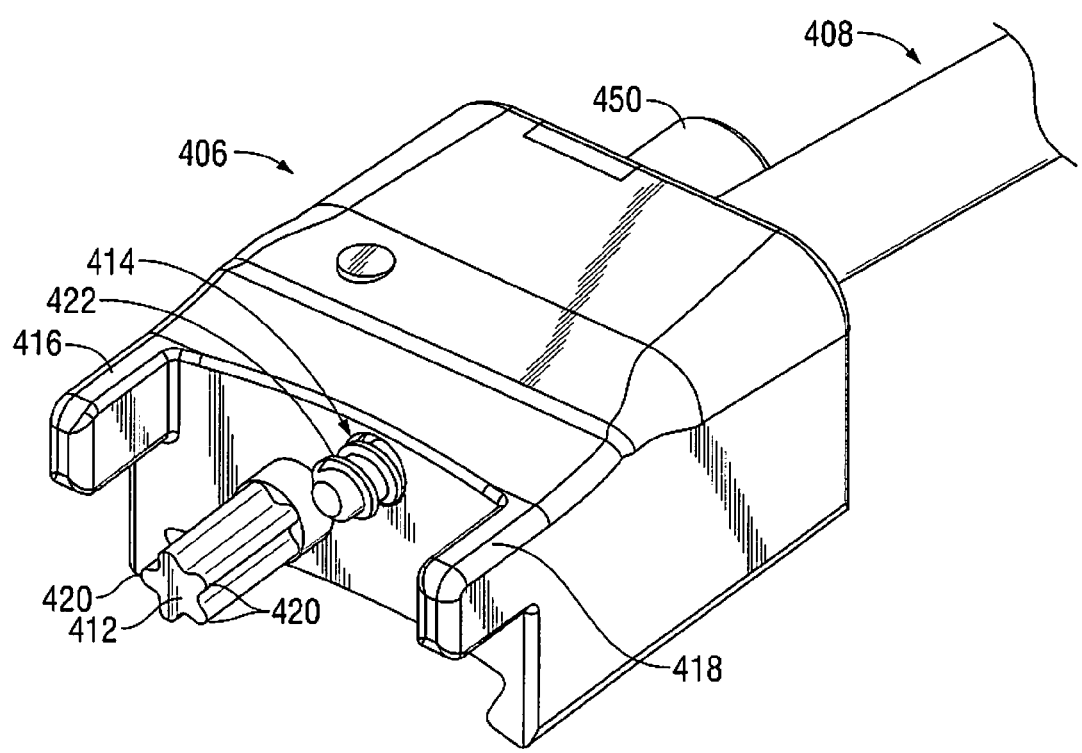
FIG. 37 is an enlarged perspective view of a distal portion of the insertion tool of FIG. 36, taken around section 37 of FIG. 36.

With reference to FIGS. 1, 4, and 7, second supporting member 14 additionally includes cavities 82, 84 positioned on opposite lateral sides 86, 88. Each cavity 82, 84 is adapted to receive arms 118 of insertion tool 100. (See FIG. 10). Second supporting member 14 also has holes 90, 92 on each lateral side 86, 88. Hole 90, which is located on lateral side 86, provides pin 40 access to slot 38, whereas hole 92, which is positioned on lateral side 88, provides pin 36 access to slot 34. (See FIG. 9). Moreover, second supporting member 14 contains an opening 94 (FIG. 7) leading to longitudinal passage 72 and another opening 96 (FIG. 7) leading to rack 66. (See also FIG. 9). Opening 94 includes an inner thread 95 (FIG. 1) and is adapted to receive pin 120 of insertion tool 100 (see FIG. 14). Further, opening 96 is configured to receive head 122 of insertion tool 100 (see FIG. 12) and threaded tip 414 of insertion tool 400 (FIG. 37). Openings 94, 96 are positioned on a front surface of second support member 14, as seen in FIG. 7.

Figure 10:
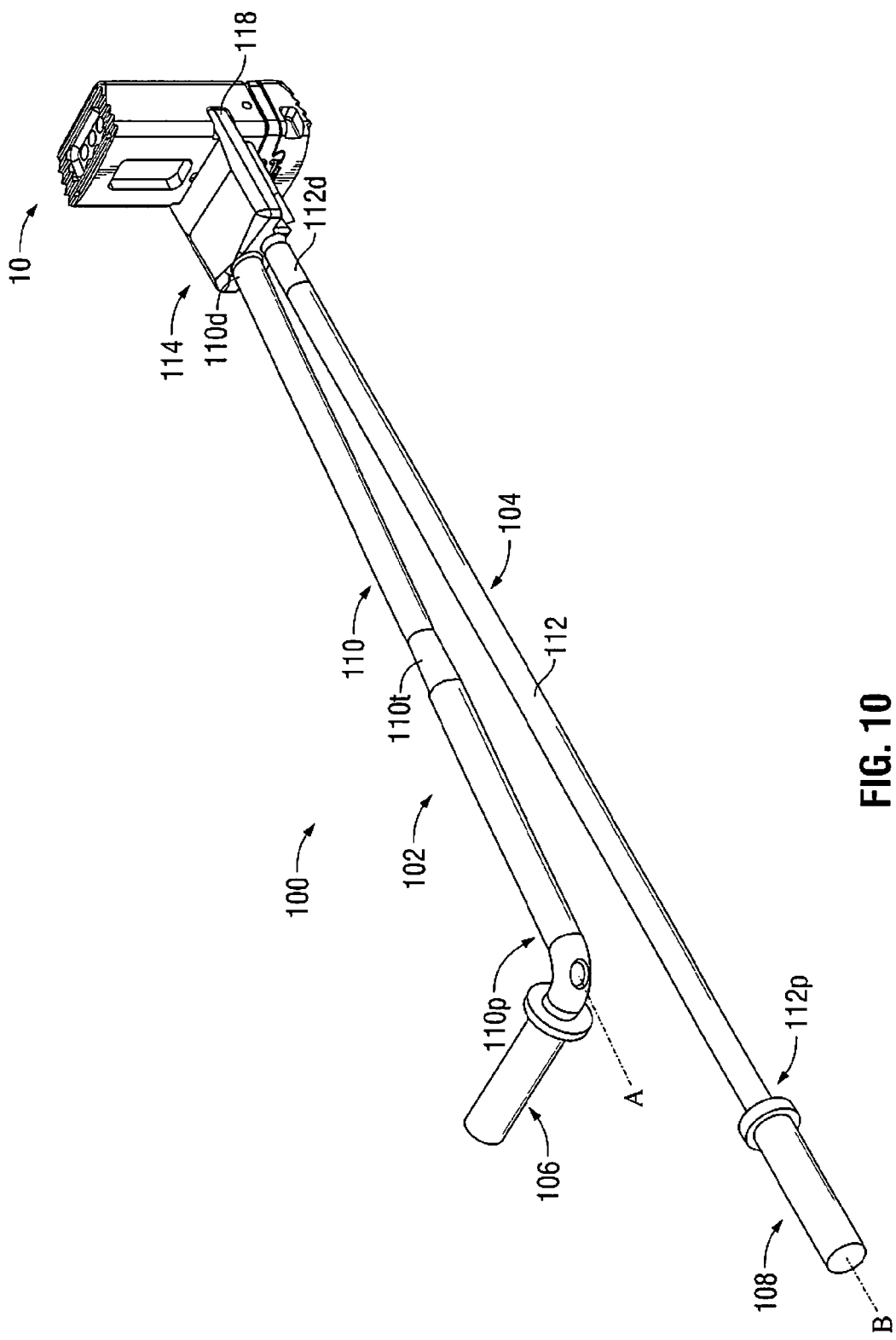
FIG. 10 is a perspective view of an insertion tool holding the expandable cage of FIG. 1 without the expandable member.
Figure 11:
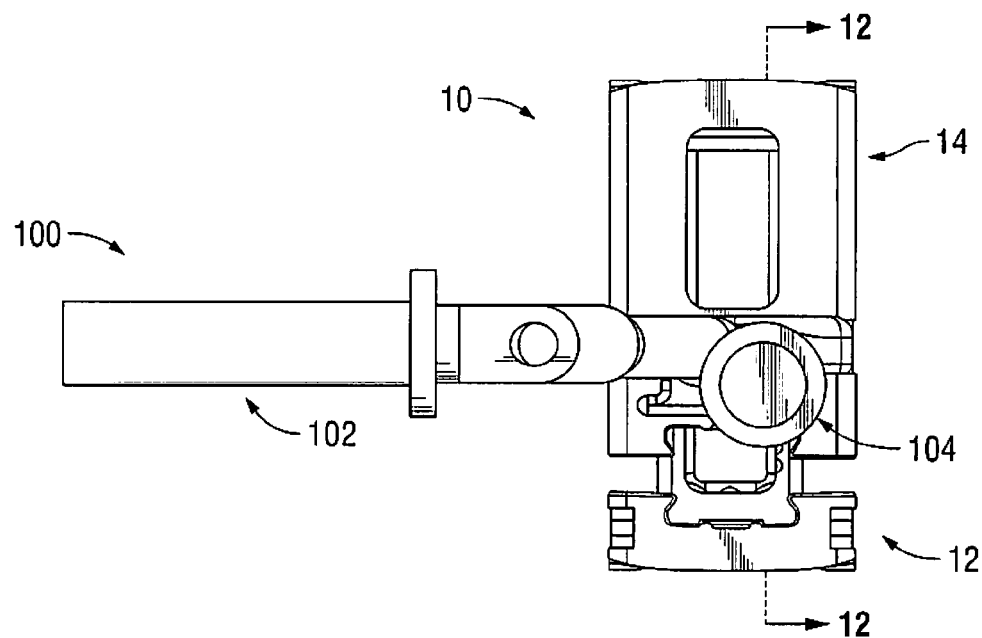
FIG. 11 is a front view of the insertion tool of FIG. 10 holding the expandable cage of FIG. 1 without the expansion member.

Referring to FIGS. 10 and 11, insertion tool 100 includes an insertion portion 102 for expanding and positioning expandable cage 10 and a driver 104 for adjusting the relative position of first and second supporting members 12, 14. Insertion portion 102 includes an elongate member 110 defining a longitudinal axis "A" and a handle 106. Elongate member 110 has a tapered section 110t. Handle 106 extends transversely from a proximal portion 110p of elongate member 110. Driver 104 includes an elongate member 112 defining a longitudinal axis "B" and a handle 108. Handle 108 extends from a proximal portion 112p of elongate body 112. Longitudinal axis "B" defines an oblique angle relative to longitudinal axis "A."

Figure 14:
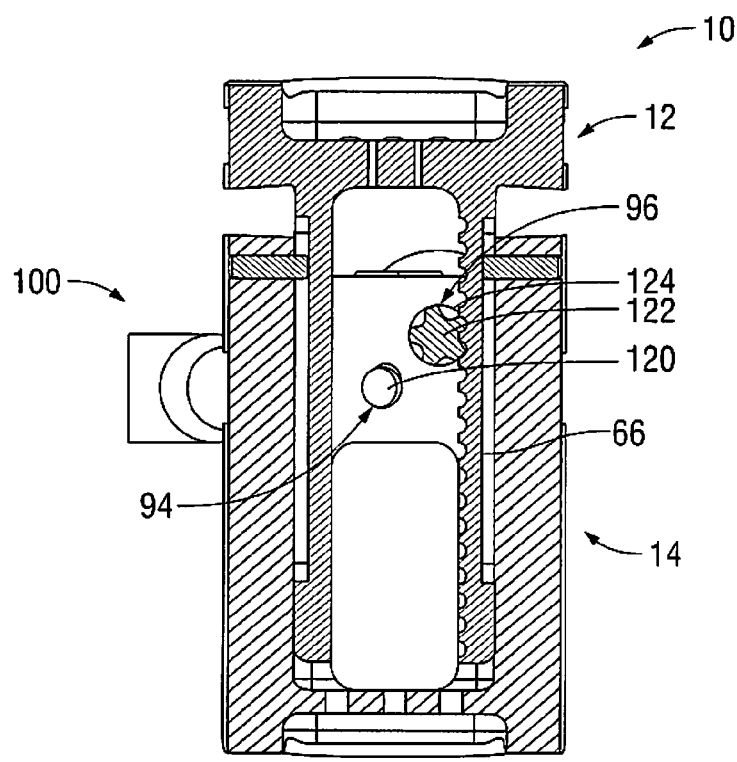
FIG. 14 is a cross-sectional view of the insertion tool of FIG. 10 holding the expandable cage of FIG. 1 without the expansion member, taken along section line 14-14 of FIG. 13.
Figure 15:
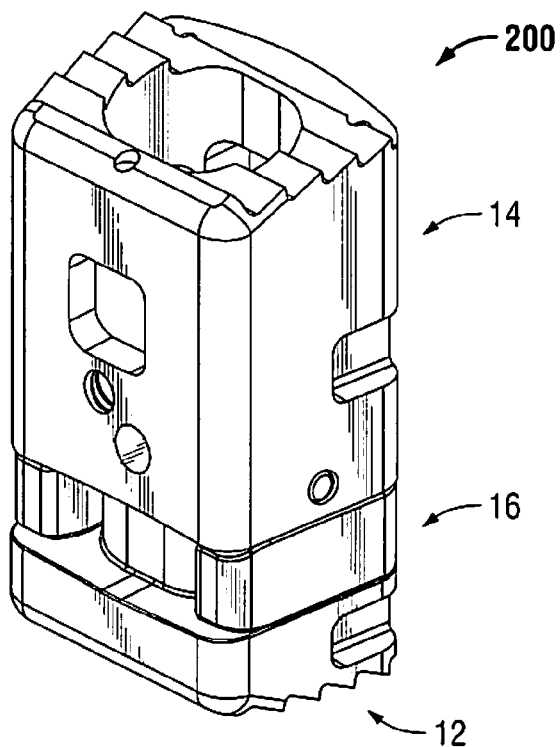
FIG. 15 is a rear perspective view of an expandable cage according to an alternate embodiment of the present disclosure with an expansion member secured between the first and second supporting members.
Figure 16:
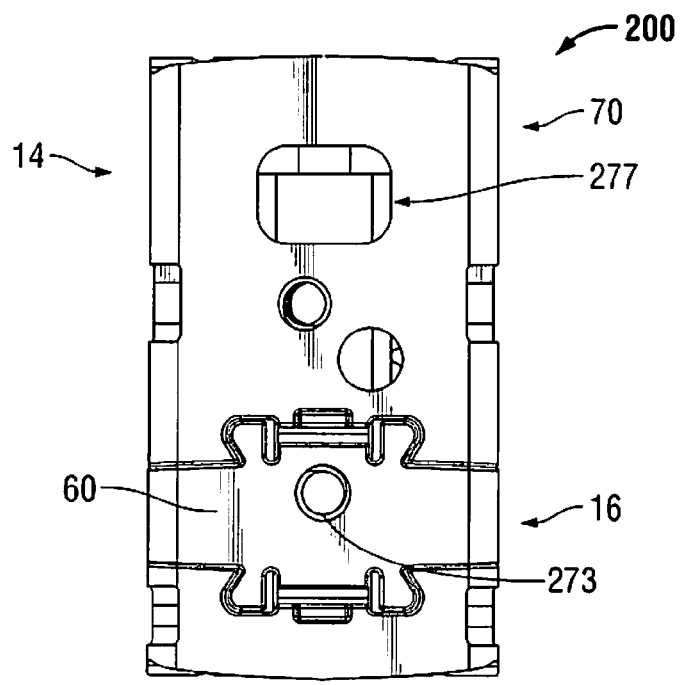
FIG. 16 is a front view of the expandable cage of FIG. 15.
Figure 17:
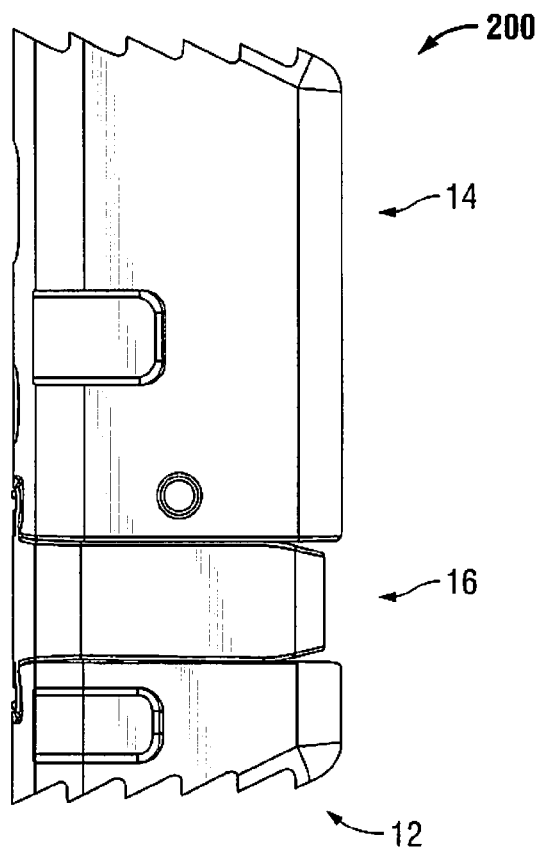
FIG. 17 is right side view of the expandable cage of FIG. 15.

Referring to FIGS. 10-14, a holding portion 114 interconnects insertion portion 102 and driver 104. Specifically, a distal end 110d of elongate member 110 is fixedly attached to holding portion 114, and a distal end 112d of elongate member 112 is rotatably connected to holding portion 114. Holding portion 114 includes a bore 116 for receiving distal end 112d of elongate member 112 and a pair of arms 118 adapted to be received within cavities 50, 52 of first supporting member 12 or cavities 82, 84 of second supporting member 14. (See FIGS. 1-4). Distal end 112d of elongate member 112 has a head 122 with a plurality of teeth 124 (FIG. 14). Head 122 is configured to be received within opening 96 of second supporting member 14. Teeth 124 are configured to engage rack 66. In operation, the rotation of head 122 causes the linear motion of rack 66. Holding portion 114 further includes a pin 120 protruding distally therefrom. Pin 120 is adapted to be received within opening 94 of second supporting member 14.

In operation, a user employs insertion tool 100 to position expandable cage 10 between adjacent vertebrae and to move first and second supporting members 12, 14 relative to each other to expand expandable cage 10. Initially, the user holds expandable cage 10 with insertion tool 100 by placing arms 118 within cavities 82, 84, pin 120 through opening 94 of second supporting member 14, and head 122 through opening 96 of second supporting member 14. After removing diseased vertebral tissue from the patient, the user advances insertion tool 100 toward the desired surgical site and places expandable cage 10 in the prepared space between vertebrae. Once expandable cage 10 has been positioned in the desired location, the user moves either first or second support member 12 or 14 relative to the other to adjust the height of expandable cage 10. To slide first and second support members 12, 14 with respect to each other, the user rotates driver 106. As driver 106 rotates, teeth 124 of head 122 engage rack 66 and cause first and second support members 12, 14 to move apart longitudinally with respect to the other. Once the desired relative position of first and second supporting members 12, 14 has been attained, the user places expansion member 16 between first and second supporting members 12, 14 to fix their relative position. The user is provided with expansion members 16 of different sizes. The user utilizes the expansion member 16 most suitable to achieve the desired expandable cage 10 height. As expandable member 16 is inserted between first and second support members 12, 14, locking portion 60 engages locking recesses 58, 64 and secures expansion member 16 to first and second supporting member 12, 14. Recesses 46, 78 may be packed with bone support matrix prior to insertion of expandable cage 10, and longitudinal recess 22 may be packed with bone support matrix material after expandable cage 10 has been positioned. Bone support matrix material may be added to expandable cage 10 through aperture 77. FIGS. 15-20 show another embodiment of the presently disclosed expandable cage 200. The construction and operation of expandable cage 200 is substantially similar to the construction and operation of expandable cage 10. In the interest of brevity, the present disclosure discusses the differences between expandable cage 200 and 10. Identical or similar reference characters designate similar or identical elements in expandable cage 10 and expandable cage 200.

Figure 24:
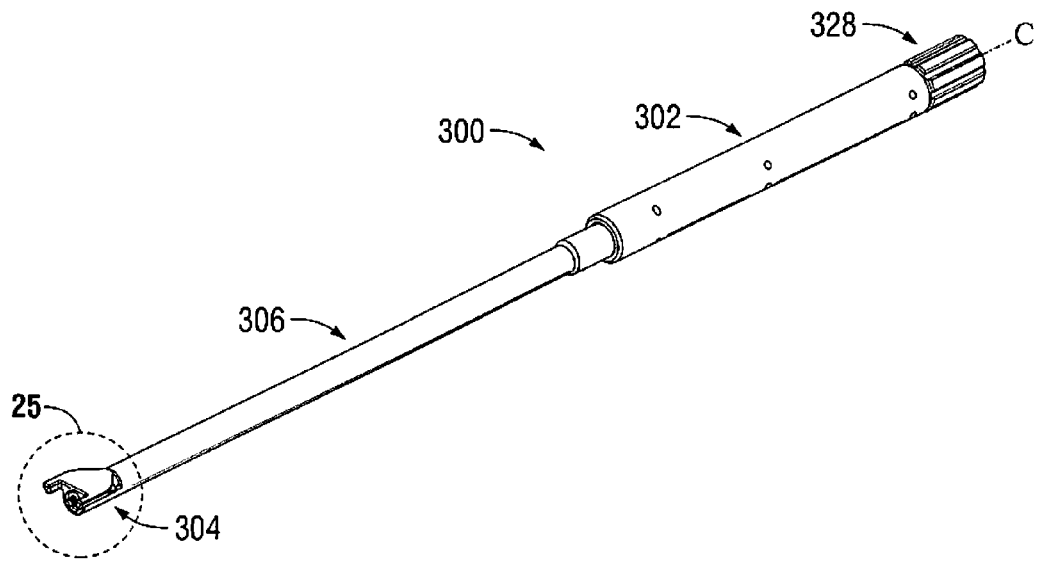
FIG. 24 is a perspective view of a driver according to an embodiment of the present disclosure.

With continued reference to FIGS. 15-20, expandable cage 200 includes an expansion member 16 substantially similar to expansion member 16 of expandable cage 10. However, expansion member 16 of expandable cage 200 includes a threaded bore 273 (FIG. 20) in lieu of opening 73 (FIG. 3) of expansion member 16 of expandable cage 10. Threaded bore 273 extends through locking portion 60 of expansion member 16 and includes an inner thread 275 (FIG. 20) adapted to mate with a threaded tip 314 of insertion tool 300 (FIG. 24). Elongate body 70 of second supporting member 14 has a rectangular aperture 277 substantially similar to rectangular aperture 77 (FIG. 2). The cross-sectional area of rectangular aperture 277 is smaller than the cross-sectional area of rectangular aperture 77 (FIG. 2).

Figure 19:
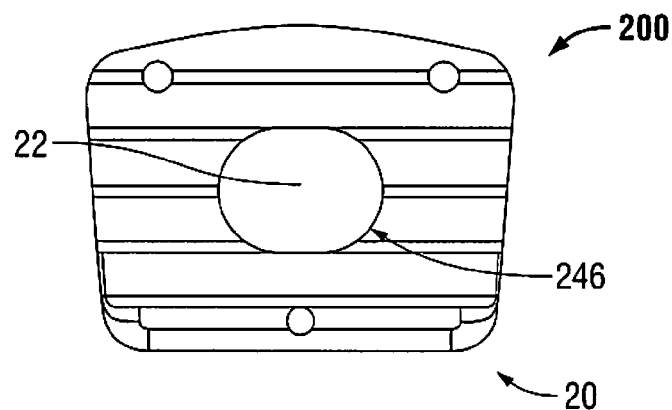
FIG. 19 is a bottom view of the expandable cage of FIG. 15.

With reference to FIG. 19, second supporting end 74 of second supporting member 14 includes an elliptical opening 278 instead of recess 78 (FIG. 6) of expandable cage 10. Elliptical opening 278 is disposed around a central area of second supporting end 74 and is adapted to allow access of bone support matrix into longitudinal passage 22.

Figure 18:
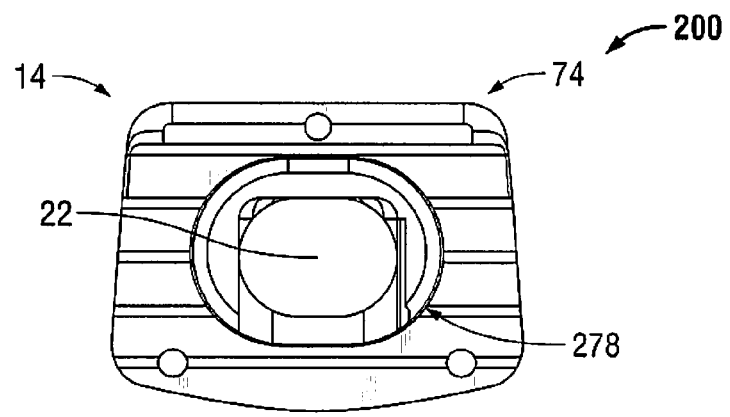
FIG. 18 is a top view of the expandable cage of FIG. 15.

Referring to FIG. 18, first supporting end 20 of first supporting member 12 includes an elliptical opening 246 instead of recess 46 (FIG. 8) of expandable cage 10. Elliptical opening 246 has a smaller cross-section than elliptical opening 278 of second supporting end 74 (FIG. 18). In addition, elliptical opening 246 is disposed around a central area of first supporting end 20 and is adapted to allow access of bone support matrix into longitudinal passage 22.

Figure 21:
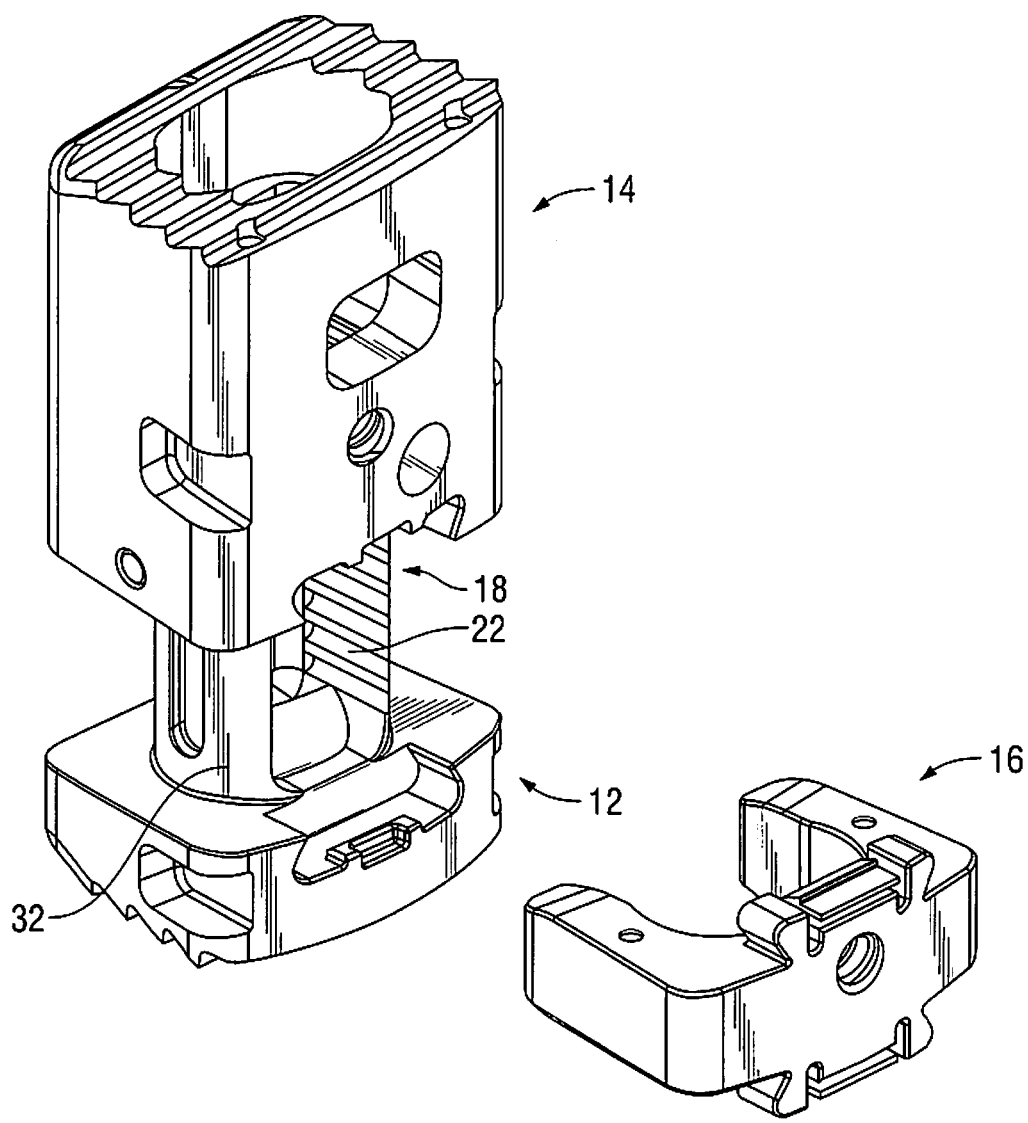
FIG. 21 is a front perspective view of the expandable cage of FIG. 15 with the expansion member separated from the expandable cage.
Figure 22:
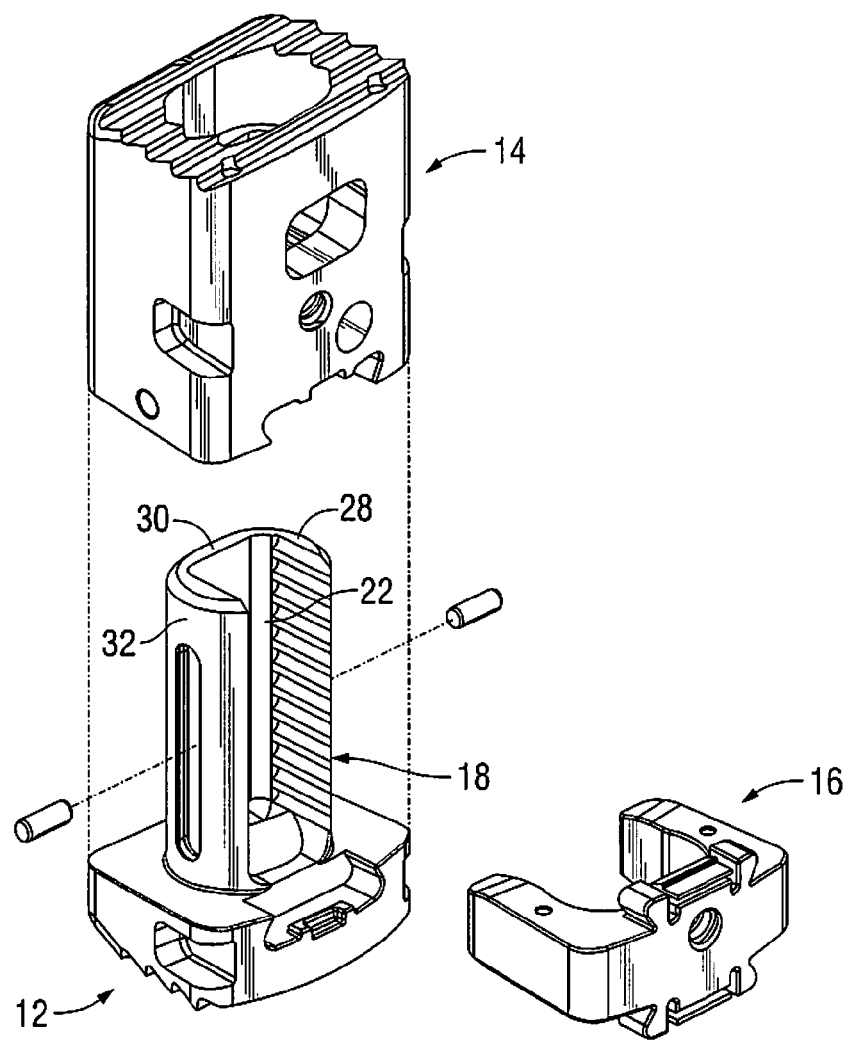
FIG. 22 is a perspective exploded view of the expandable cage of FIG. 15.
Figure 23:
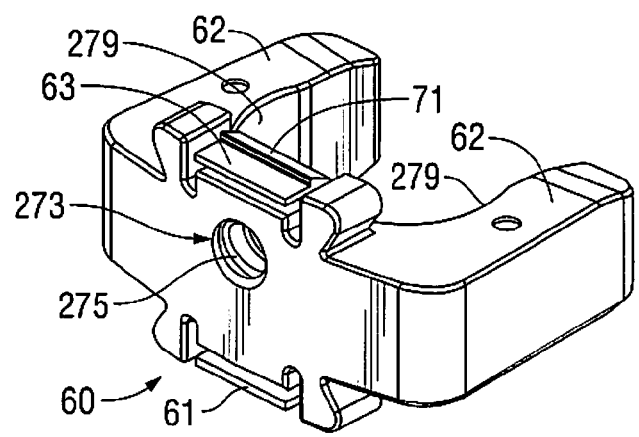
FIG. 23 is a perspective view of the expansion member of the expandable cage of FIG. 15.

As seen in FIGS. 21 and 22, first, second and third walls 28, 30, 32 of elongate body 18 have rounded outer surfaces as opposed to flat outer surfaces. First, second, and third walls 28, 30, 32 still collectively define longitudinal passage 22. As shown in FIGS. 21-23, expansion member 16 includes a locking portion 60 and pair of legs 62 extending transversely from locking portion 60. Each leg 62 includes a round inner surface 279 configured to mate with the rounded outer surfaces of walls 28, 32. Expansion member 16 of expandable cage 200 further includes a threaded hole 276 disposed through locking portion 60 and an inner thread 275 formed around threaded hole 276. Inner thread 275 is adapted to mate with an external thread 315 (FIG. 27) of threaded tip 314 of a driver 300.

Figure 25:
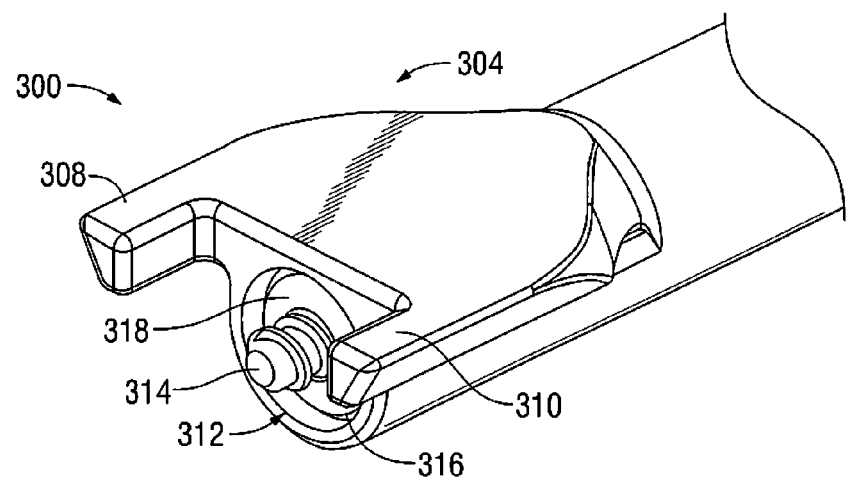
FIG. 25 is an enlarged sectional view of a distal portion of the driver of FIG. 24, taken around section 25 of FIG. 24.

FIGS. 24 and 25 illustrate another embodiment of a driver 300 for adjusting the relative position of first and second supporting members 12, 14. Driver 300, which is configured to be used in conjunction with insertion tool 400 (FIG. 36) or any other suitable insertion tool, includes a handle 302, a holding portion 304, and an elongate portion 306 interconnecting handle 302 and holding portion 304. Elongate portion 306 extends distally from handle 302 and defines a longitudinal axis "C." Holding portion 304 includes first and second arms 308, 310 extending distally therefrom, as seen in FIG. 25. First and second arms 308, 310 define a gap therebetween. In addition, holding portion 304 includes a distal opening 312 for exposing a threaded tip 314 of driver 300. Distal opening 312 is disposed in communication with a bore 316 extending through elongate portion 306. Bore 316 is configured to accommodate a tubular member 318.

Figure 20:
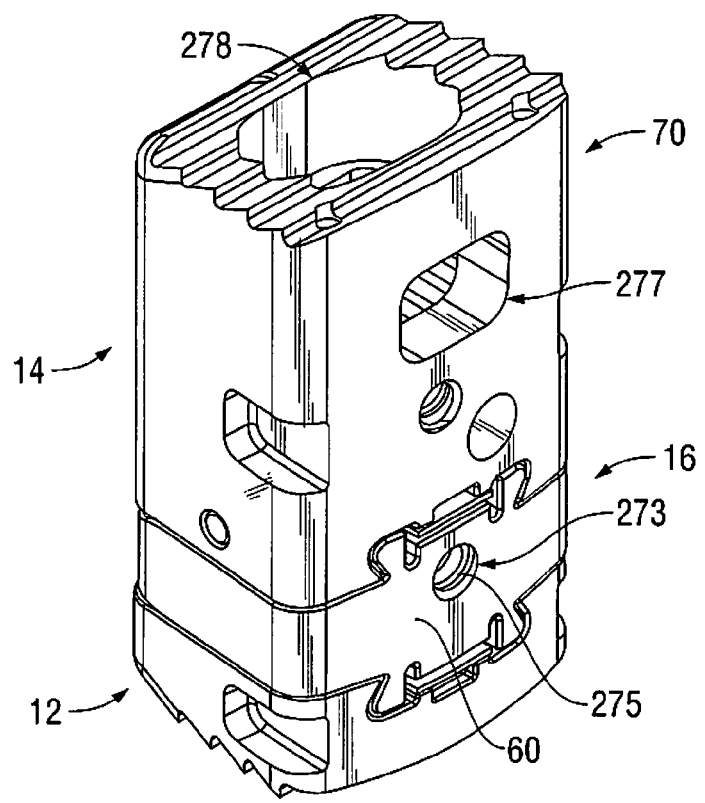
FIG. 20 is a front perspective view of the expandable cage of FIG. 15.
Figure 26:
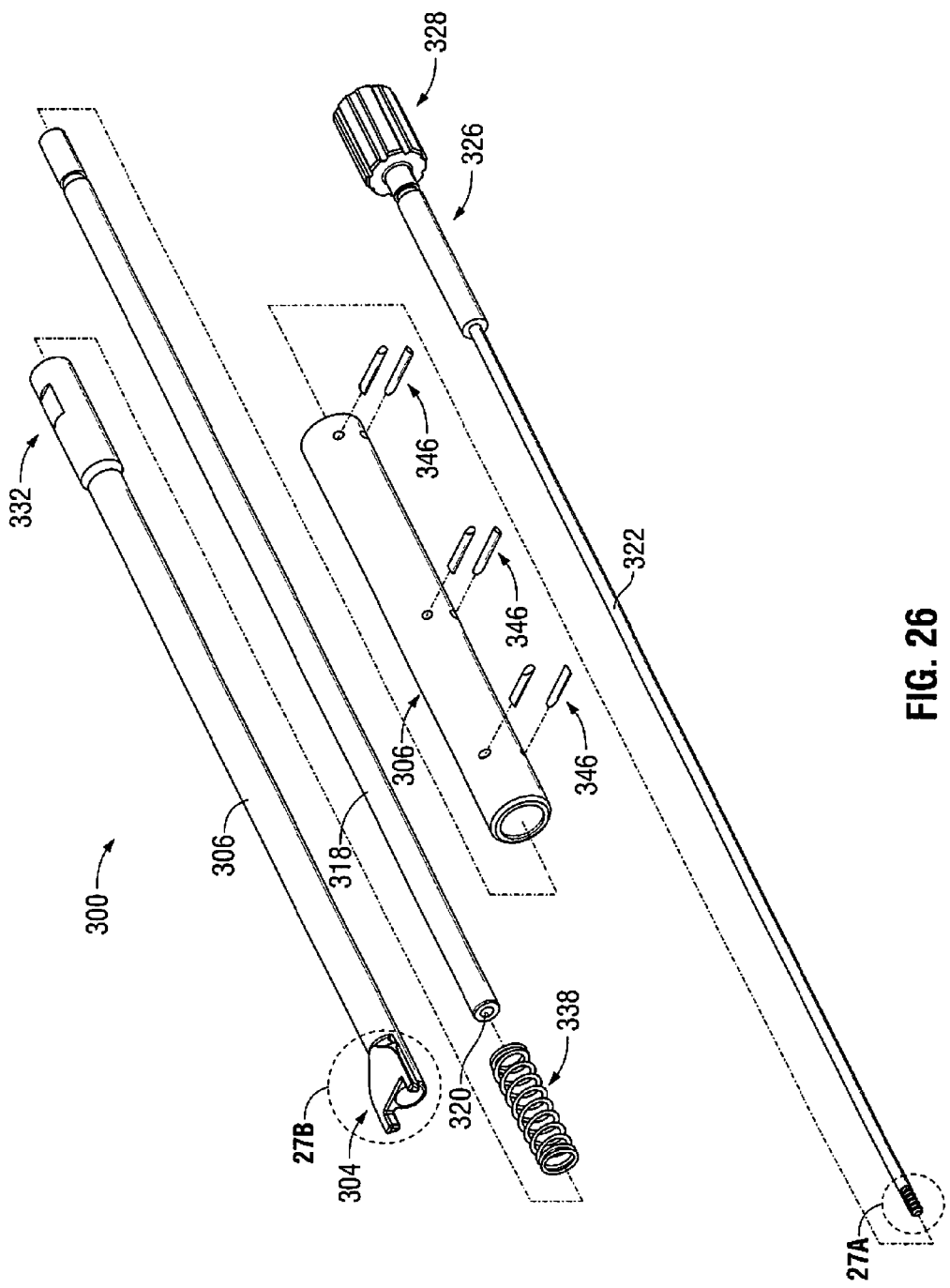
FIG. 26 is a perspective exploded view of the driver of FIG. 24.
Figure 27A:
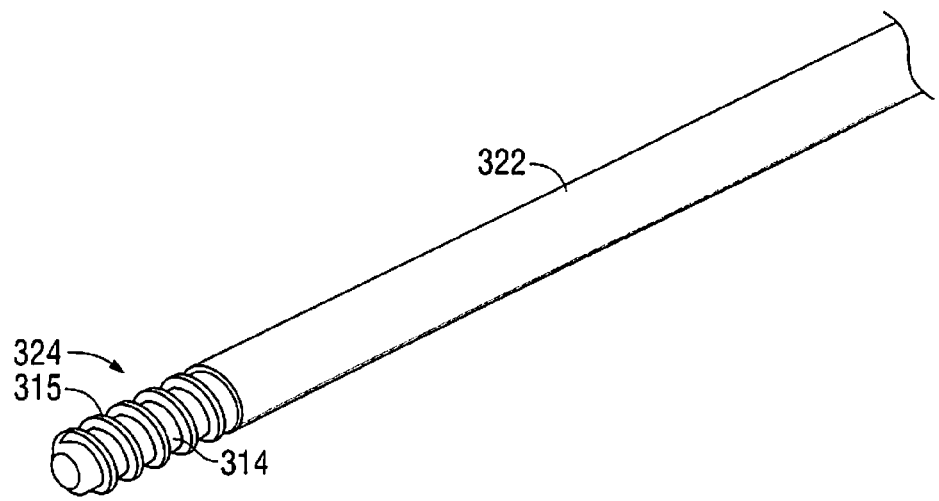
FIG. 27 is an enlarged sectional view of the distal portion of the driver of FIG. 24, taken around section 27 of FIG. 26.
Figure 27B:
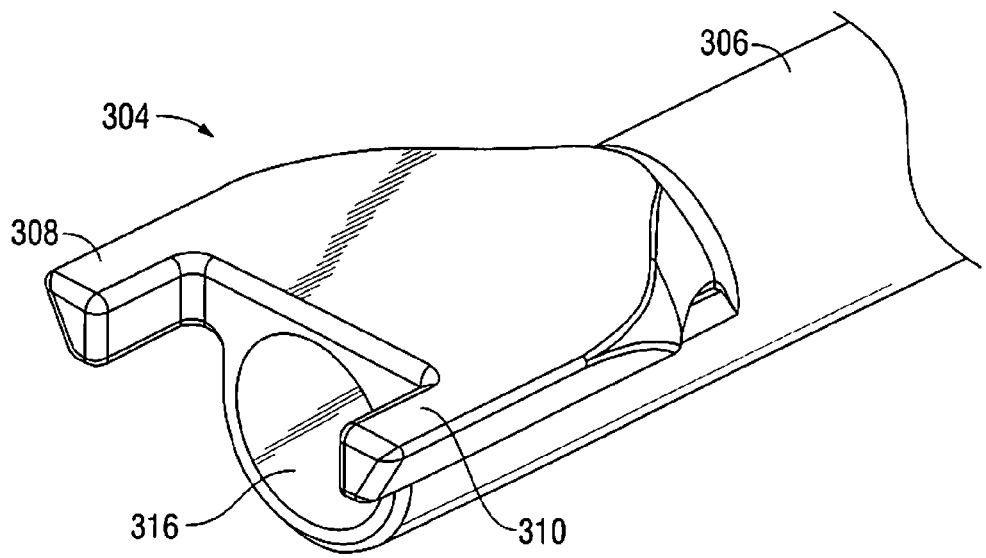

With reference to FIGS. 26 and 27, driver 300 further includes tubular member 318 having a longitudinal opening 320. Longitudinal opening 320 extends through tubular member 318 and is dimensioned to receive a rod 322. Rod 322 includes a threaded tip 314 located at a distal end 324 thereof. Threaded tip 314 includes an external thread 315 adapted to mate with inner thread 275 of threaded hole 273 of expansion member 16 (FIG. 20). A proximal end 326 of rod 322 is attached to a knob 328. Knob 328 allows a user to rotate rod 322.

Figure 30:
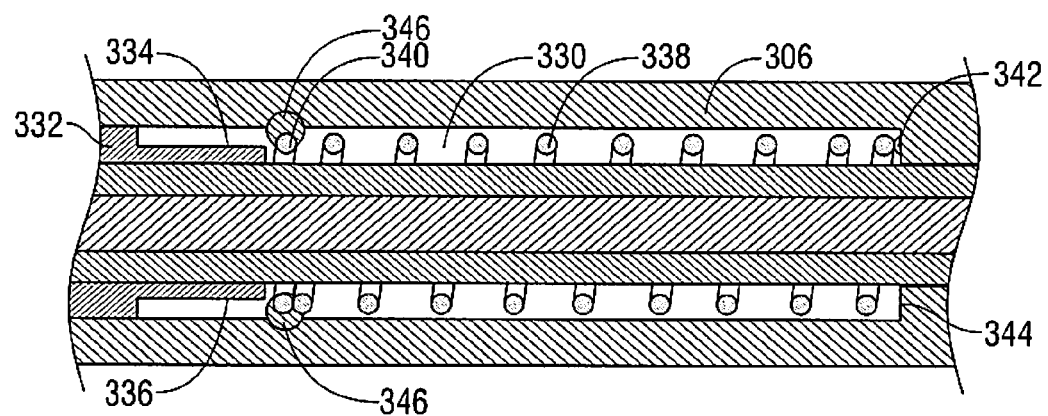
FIG. 30 is an enlarged sectional view of a proximal portion of the driver of FIG. 24; taken around section 30 of FIG. 28.
Figure 31:
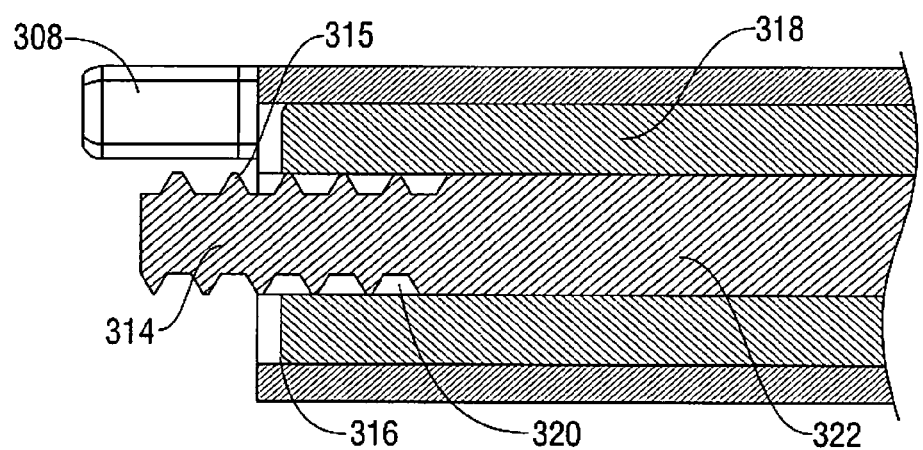
FIG. 31 is an enlarged sectional view of the distal portion of the driver of FIG. 24, taken around section 31 of FIG. 28.

Referring to FIGS. 29-31, handle 306 defines a bore 330 dimensioned to receive a proximal section 332 of elongate portion 306. Proximal section 332 of elongate portion 306 has a diameter that is larger than the diameter of the rest of elongate portion 306. Moreover, proximal section 332 of elongate portion 306 includes first and second flat surfaces 334, 336. First and second flat surfaces 334, 336 are disposed in a diametrically opposed relation relative to each other and are collectively configured to retain a distal portion 340 of a biasing member 338. In one embodiment, biasing member 338 is a coil spring, but biasing member 338 may be any suitable mechanism, apparatus, means, or device. A proximal portion 342 of biasing member 338 abuts an annular internal surface 344 of handle 306. Biasing member 338 biases rod 322 in a distal direction. A plurality of pins 346, or any other suitable apparatus, secures handle 306 to tubular member 318 and elongate portion 306.

As seen in FIG. 31, rod 322 is slidably positioned in longitudinal opening 320 of tubular member 318. Tubular member 318, in turn, is slidably disposed in bore 316 of elongate portion 306. As discussed above, biasing member 338 biases rod 322 distally so that at least a portion of threaded tip 314 is located outside of bore 316.

Figure 32:
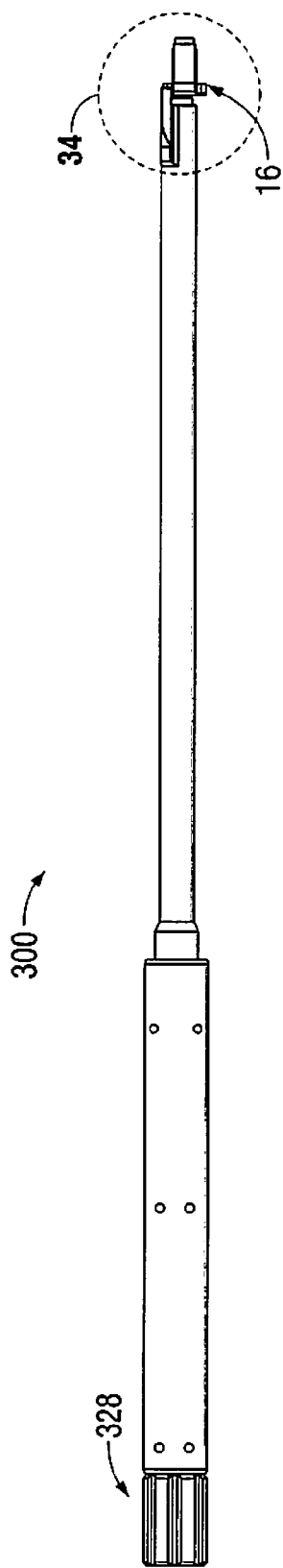
FIG. 32 is a side view of the driver of FIG. 24 holding an expansion member of FIG. 23.
Figure 33:
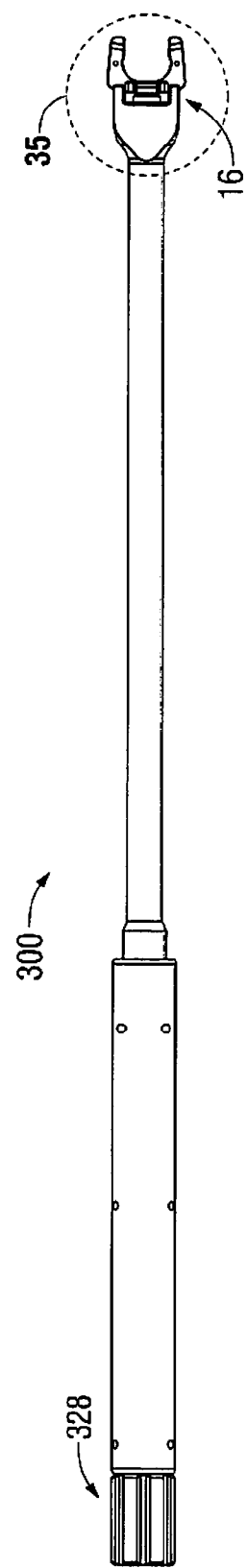
FIG. 33 is a top view of the driver of FIG. 24 holding the expansion member of FIG. 23.
Figure 34:
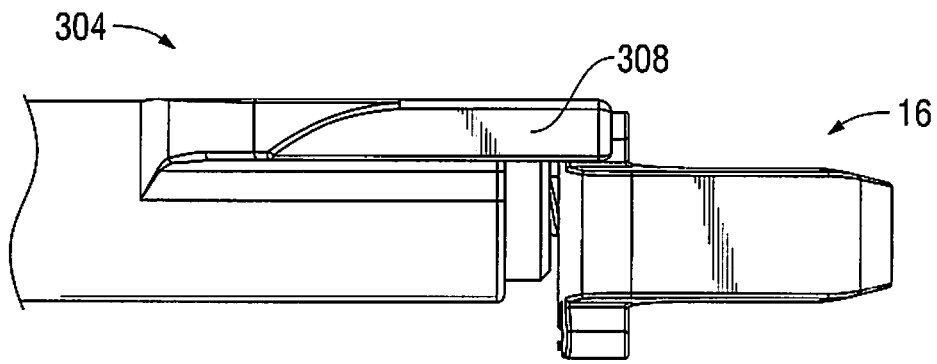
FIG. 34 is an enlarged side view of the distal portion of the driver of FIG. 24 holding the expansion member of FIG. 23, taken around section 34 of FIG. 32.
Figure 35:
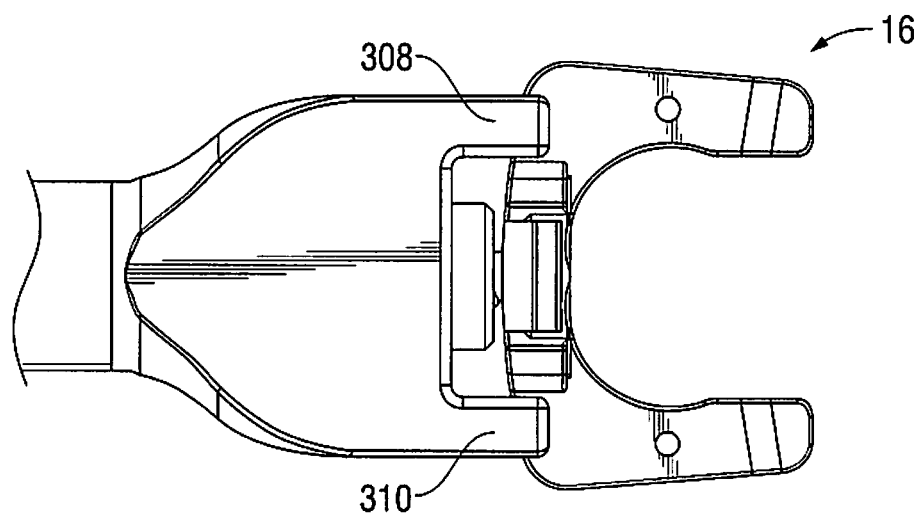
FIG. 35 is an enlarged top view of the distal portion of the driver of FIG. 24 holding the expansion member of FIG. 23, taken around section 35 of FIG. 33.

As seen in FIGS. 32-33, driver 300 can be employed, among other things, for holding and inserting expansion member 16 of expandable cage 200 between first ands second supporting members 12, 14. As discussed above, expansion member 16 of expandable cage 200 includes a threaded bore 273 having inner thread 275 (FIG. 20), and driver 300 includes a threaded tip 314 having an external thread 315. Inner thread 275 is adapted to mate with external thread 315 of threaded tip 314. In operation, a user inserts at least a portion of threaded tip 314 of driver 300 in threaded hole 237 of expansion member 16. At this moment, first and second arms 308, 310 abut an upper surface of expansion member 16, as seen in FIG. 34. Then, the user rotates rod 322 (FIG. 26) via knob 328 to rotate threaded tip 314. In response to the rotation of threaded tip 314, external thread 315 of threaded tip 314 threadably engages inner thread 275 of threaded hole 237, thus securing expansion member 16 to driver 300. After expansion member 16 has been secured to driver 300, the user advances driver 300 toward first and second supporting members 12, 14 and places expansion member 16 between first and second supporting members 12, 14. As discussed in detail below, driver 300 can also be used in conjunction with insertion tool 400 (FIG. 36) which displaces first and second supporting members 12, 14 relative to each other in preparation to receive expansion member 16.

Figure 36:
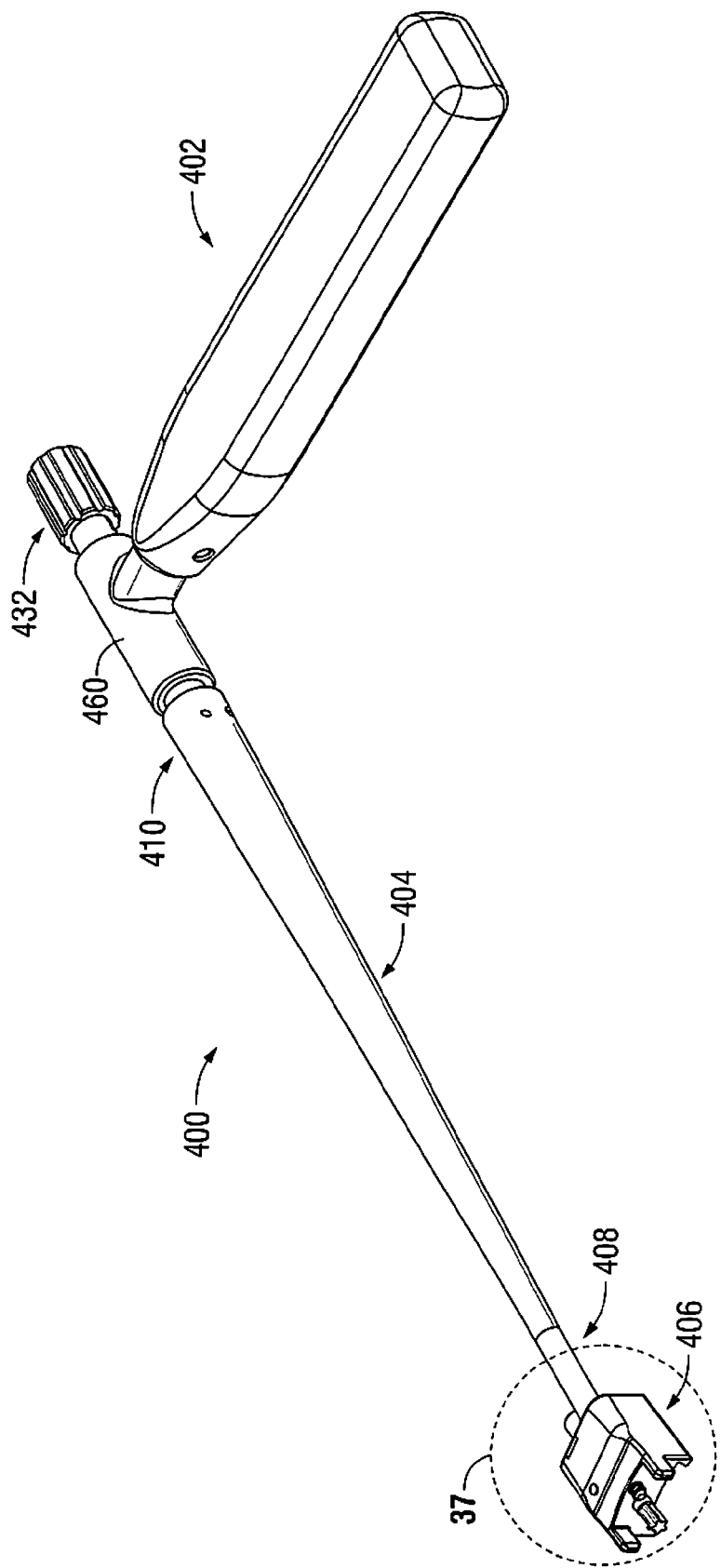
FIG. 36 is a perspective view of an insertion tool according to another embodiment of the present disclosure.

FIGS. 36 and 37 show an insertion tool 400 designed for inserting expandable cage 10 inside into a prepared space in the body. Specifically, a user may utilize insertion tool 400 to place expandable cage 10 between vertebrae. Insertion tool 400 generally includes a handle 402, an elongate section 404 oriented transversely relative to handle 402, and a holding section 406 attached to a distal portion 408 of elongate section 404. Handle 402 facilitates gripping by a user and is operably coupled to a proximal portion 410 of elongate section 404.

As depicted in FIG. 37, holding section 406 is adapted to hold expandable cage 10 and includes a hexalobular head 412 rotatably mounted thereon, a threaded tip 414 also rotatably mounted thereon, and first and second arms 416, 418 extending distally therefrom. Hexalobular head 412 includes teeth 420 each configured to engage undulations 42 of rack 66 of first support member 12 (FIGS. 3 and 9). As discussed in detail below, rotating hexalobular head 412 when teeth 420 are engaged with undulations 42 of rack 66 causes first and second supporting members 12, 14 to move relative to each other. Threaded tip 414 is dimensioned to be received within opening 94 and includes an external thread 422 formed thereabout. External thread 422 of threaded tip 414 is adapted to mate inner thread 95 of opening 94 of first support member 12 (FIG. 1) to secure holding section 406 of insertion tool 400 to expandable cage 10 (FIG. 1). First and second arms 416, 418 define a gap therebetween. Each of first and second arms 416, 418 is configured to be received in cavities 82, 84 of expandable cage 10 (FIGS. 1 and 4). When first and second arms 416, 418 are positioned in cavities 82, 84 of expandable cage 10 (FIGS. 1 and 4), holding section 406 retains expandable cage 10.

Figure 38:
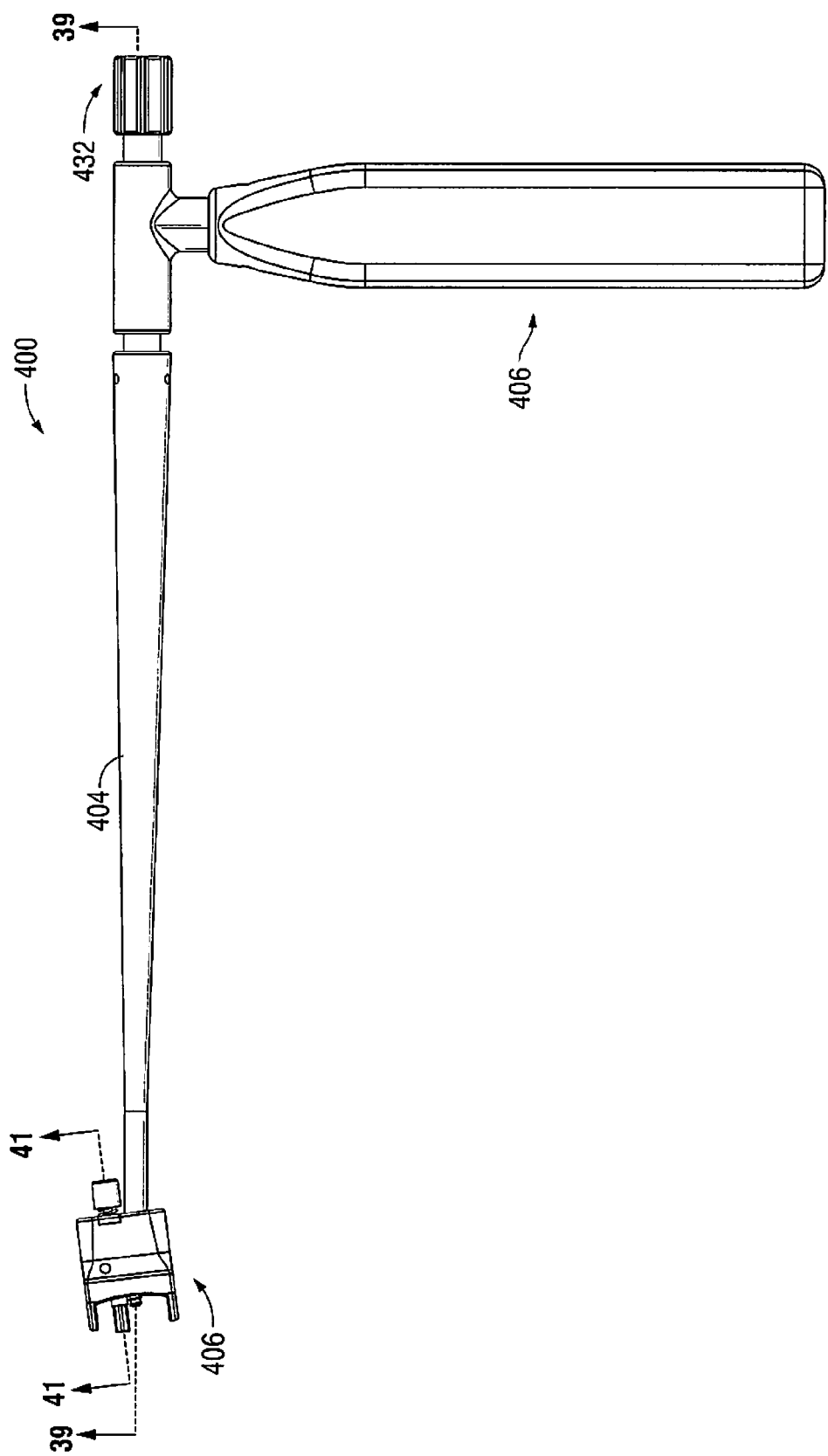
FIG. 38 is a side view of the insertion tool of FIG. 36.
Figure 39:
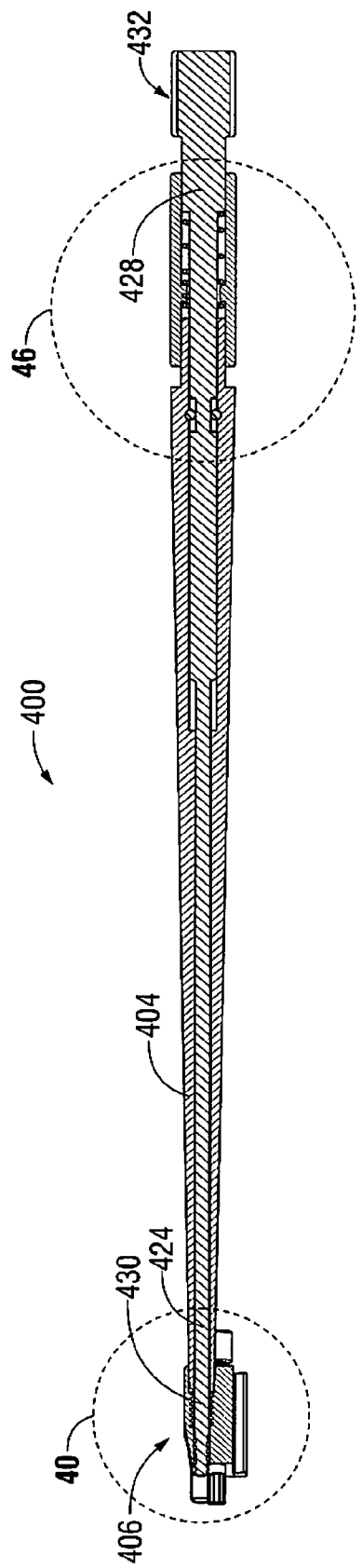
FIG. 39 is a side cross-sectional view of the insertion tool of FIG. 35, taken along section line 39-39 of FIG. 38.
Figure 40:
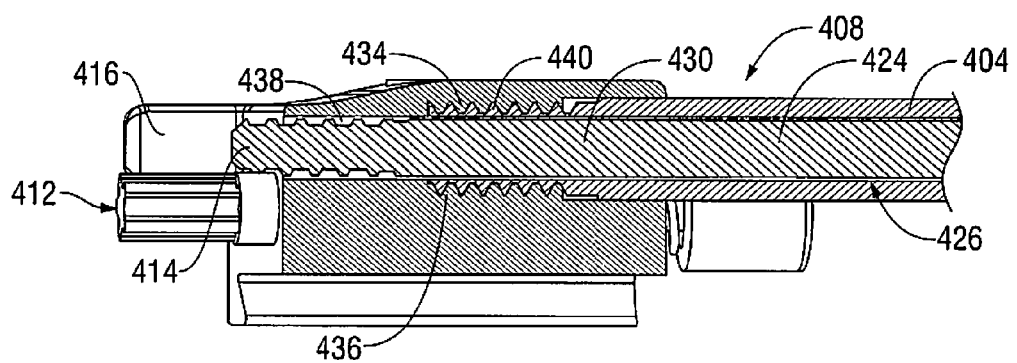
FIG. 40 is an enlarged side cross-sectional view of the distal portion of the insertion tool of FIG. 36, taken around section 40 of FIG. 39.
Figure 41:
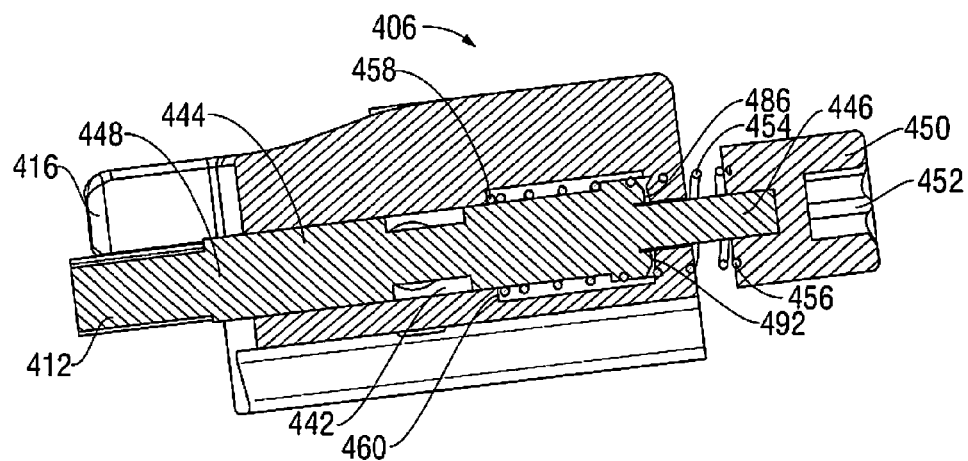
FIG. 41 is a side cross-sectional view of the distal portion of the insertion tool of FIG. 36, taken along section line 41-41 of FIG. 38.
Figure 42:
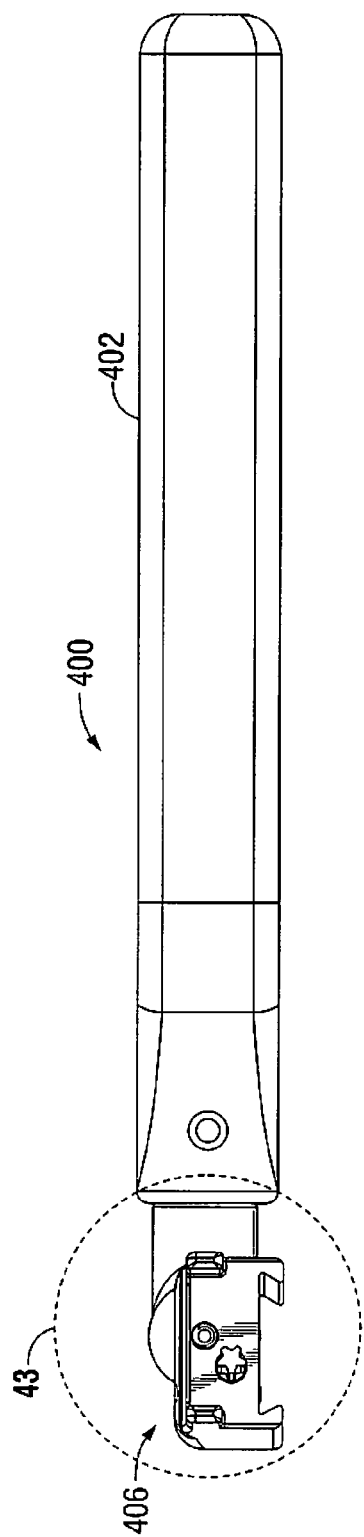
FIG. 42 is a front view of the insertion tool of FIG. 36.
Figure 43:
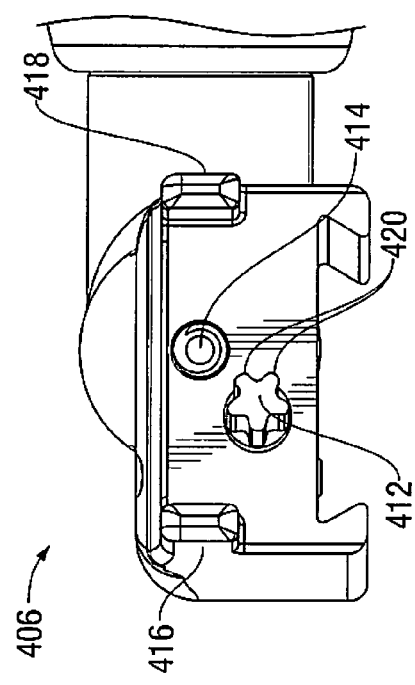
FIG. 43 is an enlarged front view of the insertion tool of FIG. 36, taken around section 43 of FIG. 42.
Figure 44:
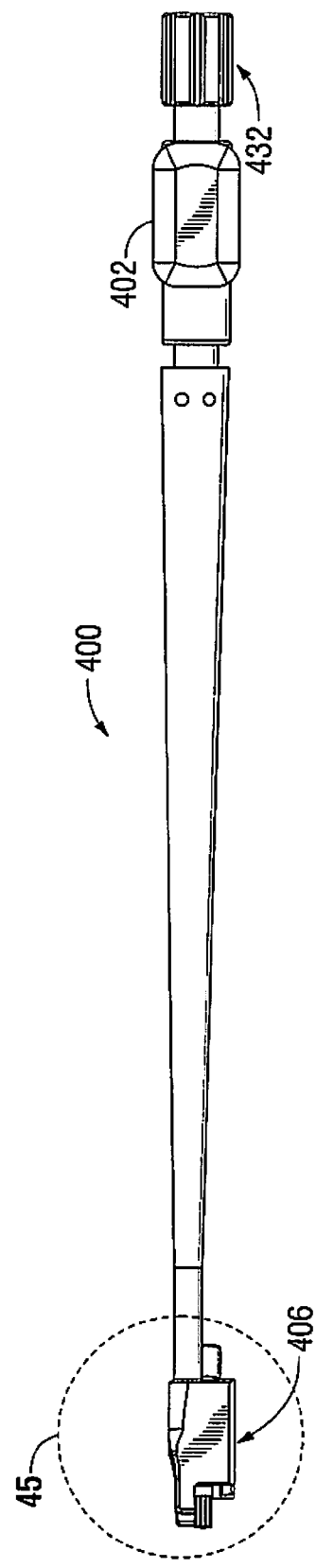
FIG. 44 is a side view of the insertion tool of FIG. 36.
Figure 45:
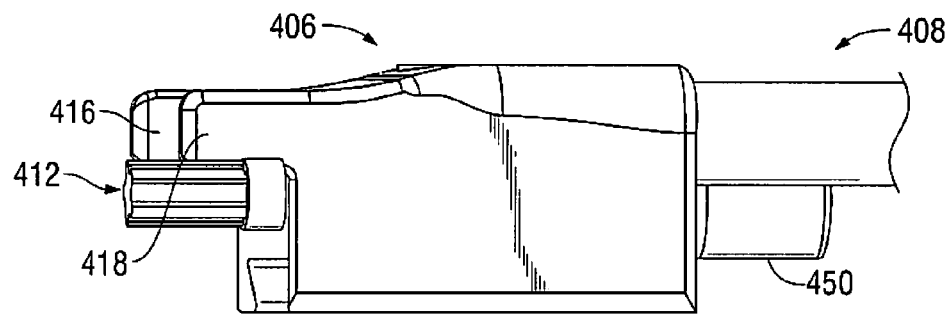
FIG. 45 is an enlarged side view of the distal portion of the insertion tool of FIG. 44, taken around section 45 of FIG. 44.

With reference to FIGS. 38-40, insertion tool 400 includes a rod 424 slidably disposed through elongate section 404. Elongate section 404 has a longitudinal opening 426 extending therethrough. Longitudinal opening 426 of elongate section 404 is dimensioned to slidably receive rod 424. Rod 424 has a proximal portion 428 and a distal portion 430. A knob 432 is attached to proximal portion 428 of rod 424. Distal portion 430 of rod 424 is connected to threaded tip 414.

As seen in FIG. 40, elongate section 404 includes a thread 434 disposed around distal portion 408. Thread 434 is adapted to mate with an inner thread 436 of holding section 406. When thread 434 of elongate section 404 mates with inner thread 436 of holding section 406, elongate section 404 attaches to holding section 406.

As illustrated in FIG. 40, holding section 406 includes a first bore 438 dimensioned to receive distal portion 430 of rod 424, at least part of distal portion 408 of elongate section 404, and threaded tip 414. Holding section 406 further includes a thread 440 formed around a portion of first bore 438. Thread 440 is adapted to mate with thread 434 of rod 424 to fix the position of rod 424 relative to holding section 406.

With reference to FIGS. 41-45, holding section 406 includes a second bore 442 oriented at an oblique angle relative to first bore 438 (FIGS. 38 and 40). Second bore 442 is dimensioned to slidably receive a bar 444. Bar 444 has a proximal portion 446 and a distal portion 448. Distal portion 448 of bar 444 is attached to hexalobular head 412, and proximal portion 446 of bar 444 is connected to a cylindrical member 450. Cylindrical member 450 includes a socket 452 configured to receive and engage threaded tip 314 of driver 300 as described in greater detail below with reference to FIGS. 49-53. Bar 444 is rotatably disposed in bore 442 such that, when threaded tip 314 of driver 300 engages socket 452, rotating threaded tip 314 causes the rotation of bar 444. Holding section 406 further includes a biasing member 454, such as a spring, partially positioned inside bore 442. Biasing member 454 includes a proximal end 456 attached to cylindrical member 450 and a distal end 458 abutting an inner annular wall 460 of holding section 406. In operation, biasing member 454 biases bar 444 proximally.

Figure 46:
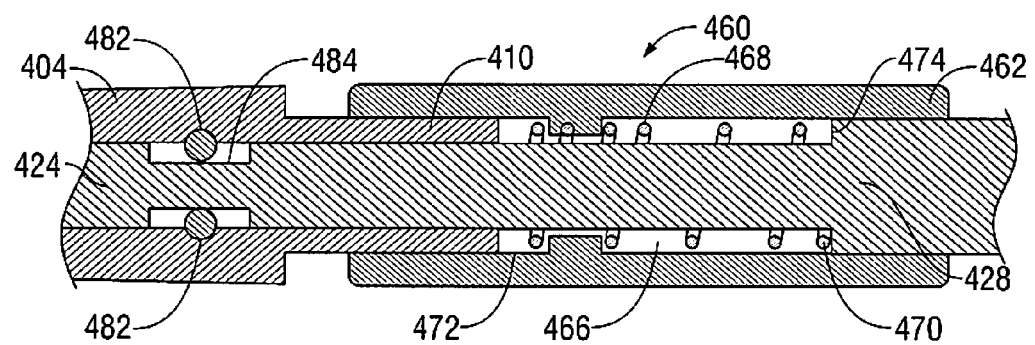
FIG. 46 is a side cross-sectional view of a proximal portion of the insertion tool of FIG. 36, taken around section 46 of FIG. 39.
Figure 47:
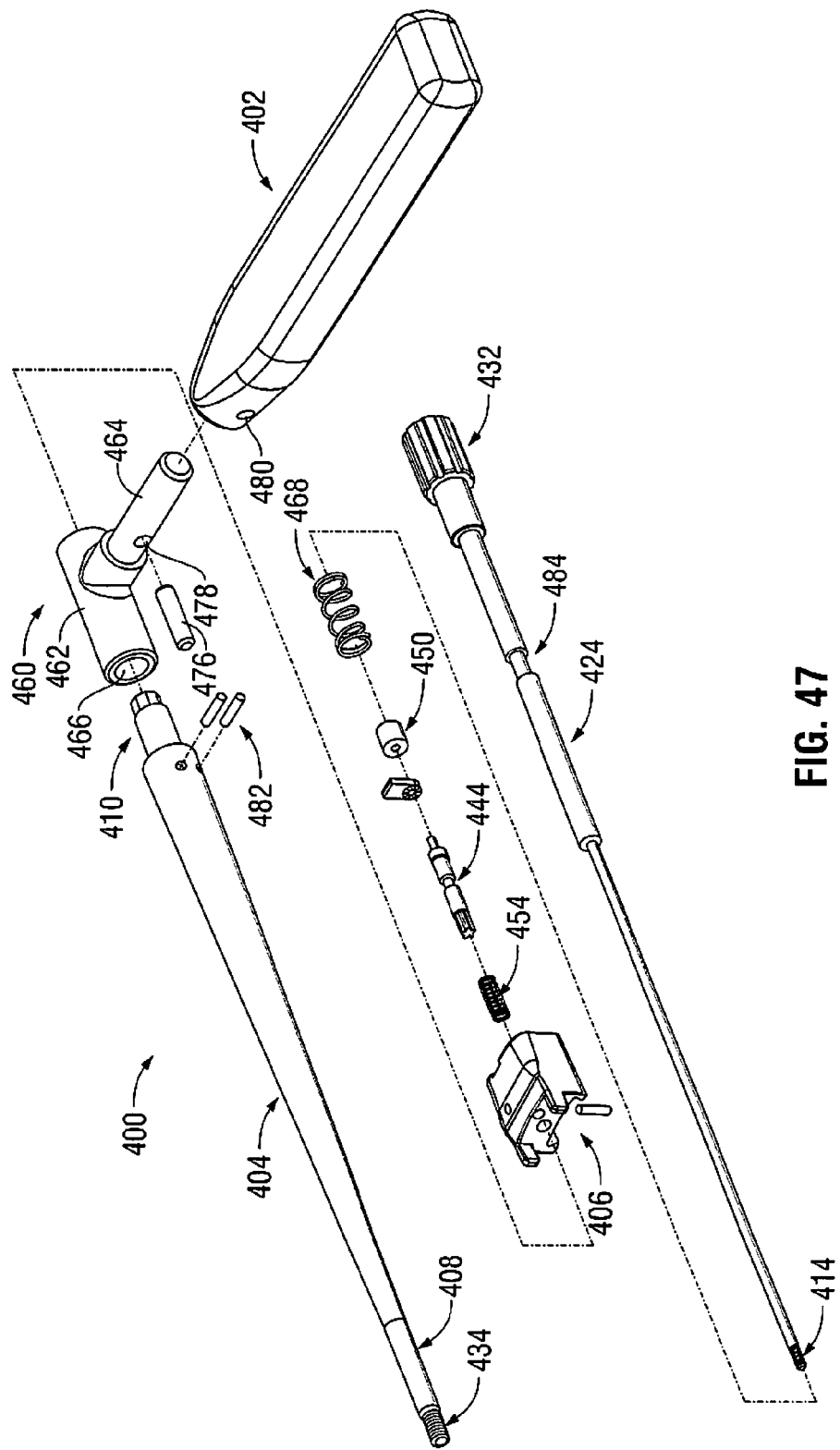
FIG. 47 is a perspective exploded view of the insertion tool of FIG. 36.

With reference to FIGS. 46 and 47, insertion tool 400 further includes a coupling member 460 for connecting handle 402 to elongate section 404. Coupling member 460 includes a tubular portion 462 and shaft 464 extending transversely from tubular portion 462. As shown in FIG. 46, tubular portion 462 defines a longitudinal opening 466 extending therethrough. Longitudinal opening 466 is configured to receive at least part of proximal portion 410 of elongate section 404 and at least part of proximal portion 428 of rod 424. A biasing member 468, such as a spring, partially surrounds proximal portion 428 of rod 424 and has a proximal end 470 and a distal end 472. Proximal end 470 of biasing member 468 abuts an annular wall 474 located on proximal portion 428 of rod 424. Distal end 472 of biasing member 468 is attached to proximal portion 410 of elongate section 404. Biasing member 468 is disposed in longitudinal opening 466 of tubular portion 462, and in operation, biases rod 424 in a proximal direction.

As seen in FIG. 47, shaft 464 of coupling member 460 is positioned inside handle 402. A pin 476, or any other suitable device, apparatus, or means, couples handle 406 to shaft 464, thereby connecting handle 402 to coupling member 460. Shaft 464 includes a hole 478 adapted to receive pin 476. Handle 402 also includes a hole 480 adapted to receive pin 476. When pin 476 is inserted through hole 480 of handle 402 and hole 478 of shaft 464, pin 476 interconnects handle 402 and coupling member 460.

With continued reference to FIGS. 46 and 47, insertion tool 400 additionally includes a plurality of pins 482 for connecting rod 424 to elongate section 404. (See also FIG. 46). Rod 424 includes a depressed area 484 having a smaller diameter than the surrounding portions of rod 424. When insertion tool 400 is assembled, pins 482 seat on diametrically opposed sides of depressed area 484 to secure rod 424 to elongate section 404. (See FIG. 46).

Figure 48:
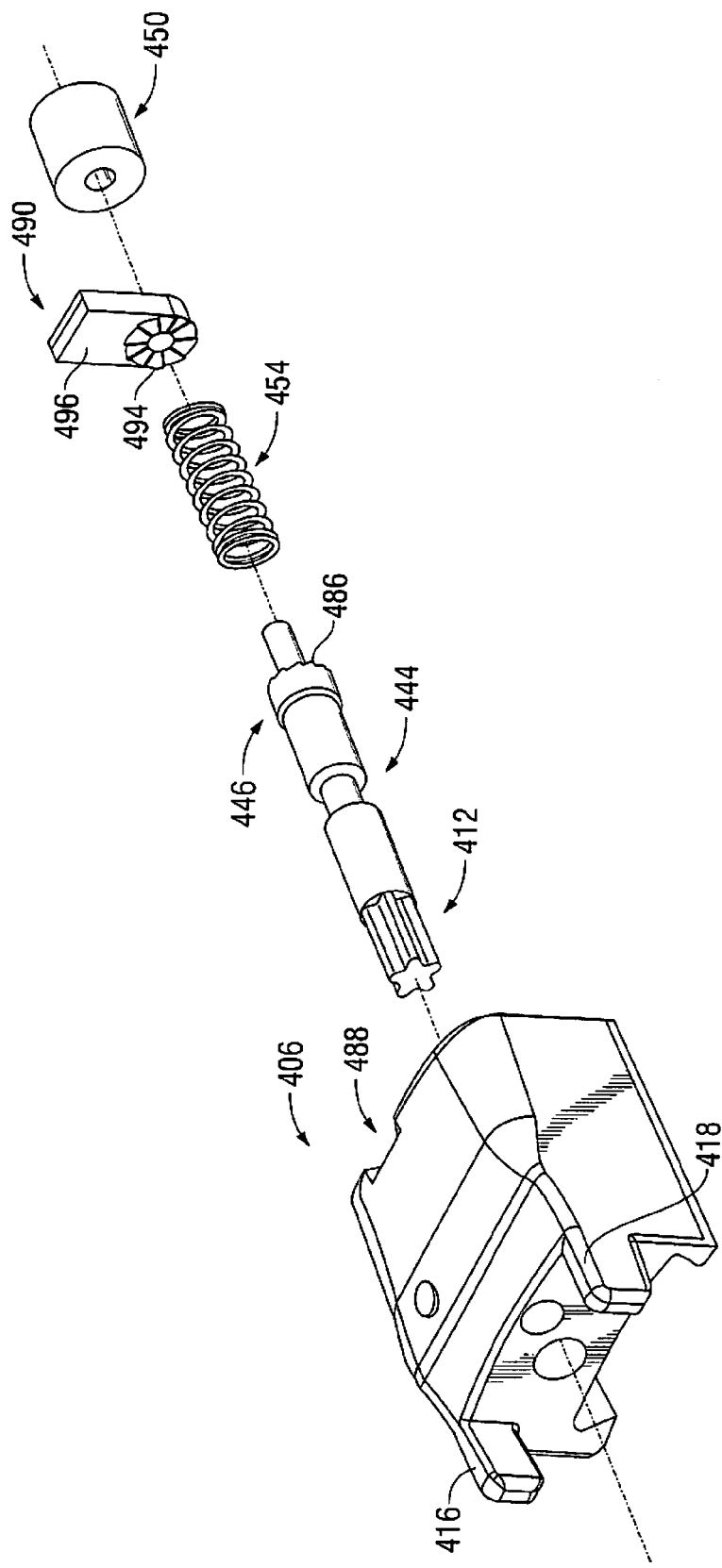
FIG. 48 is a perspective exploded view of the distal portion of the insertion tool of FIG. 36.
Figure 49:
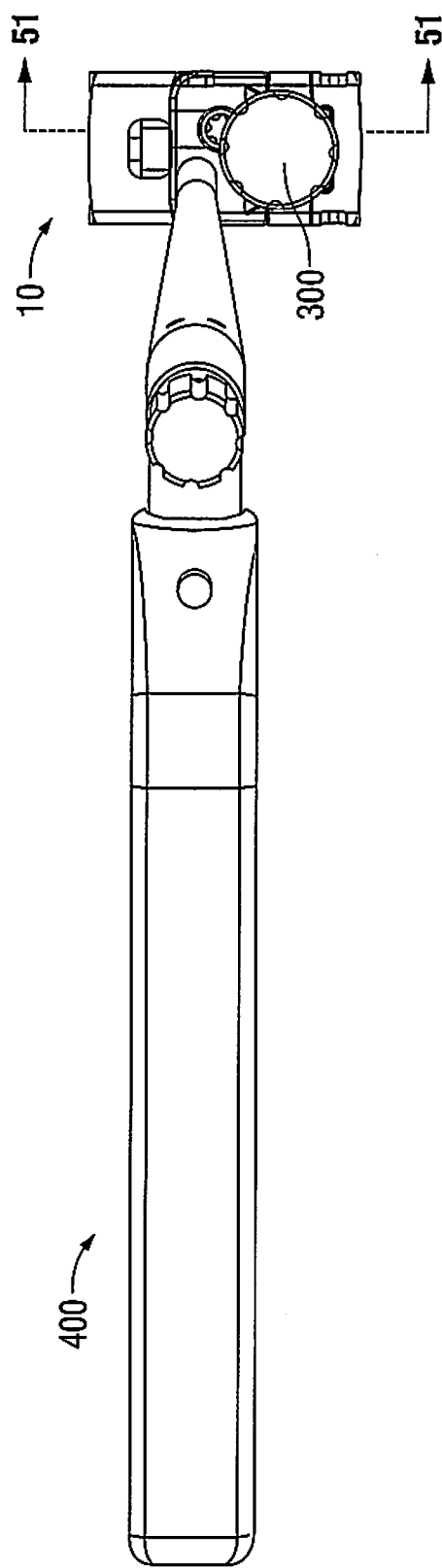
FIG. 49 is a rear view of the insertion tool of FIG. 36 holding the expandable cage of FIG. 15.
Figure 50:
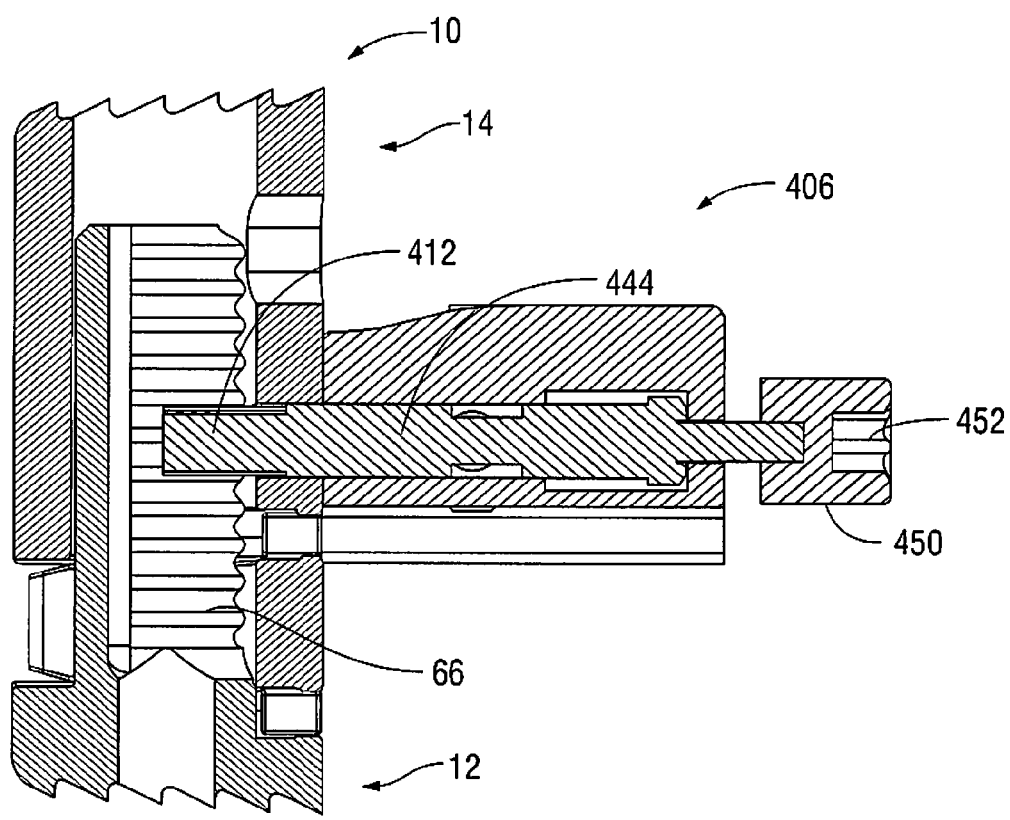
FIG. 50 is a side cross-sectional view of the distal portion of the insertion tool of FIG. 36 holding the expandable cage of FIG. 15, taken around section 52 of FIG. 51.
Figure 51:
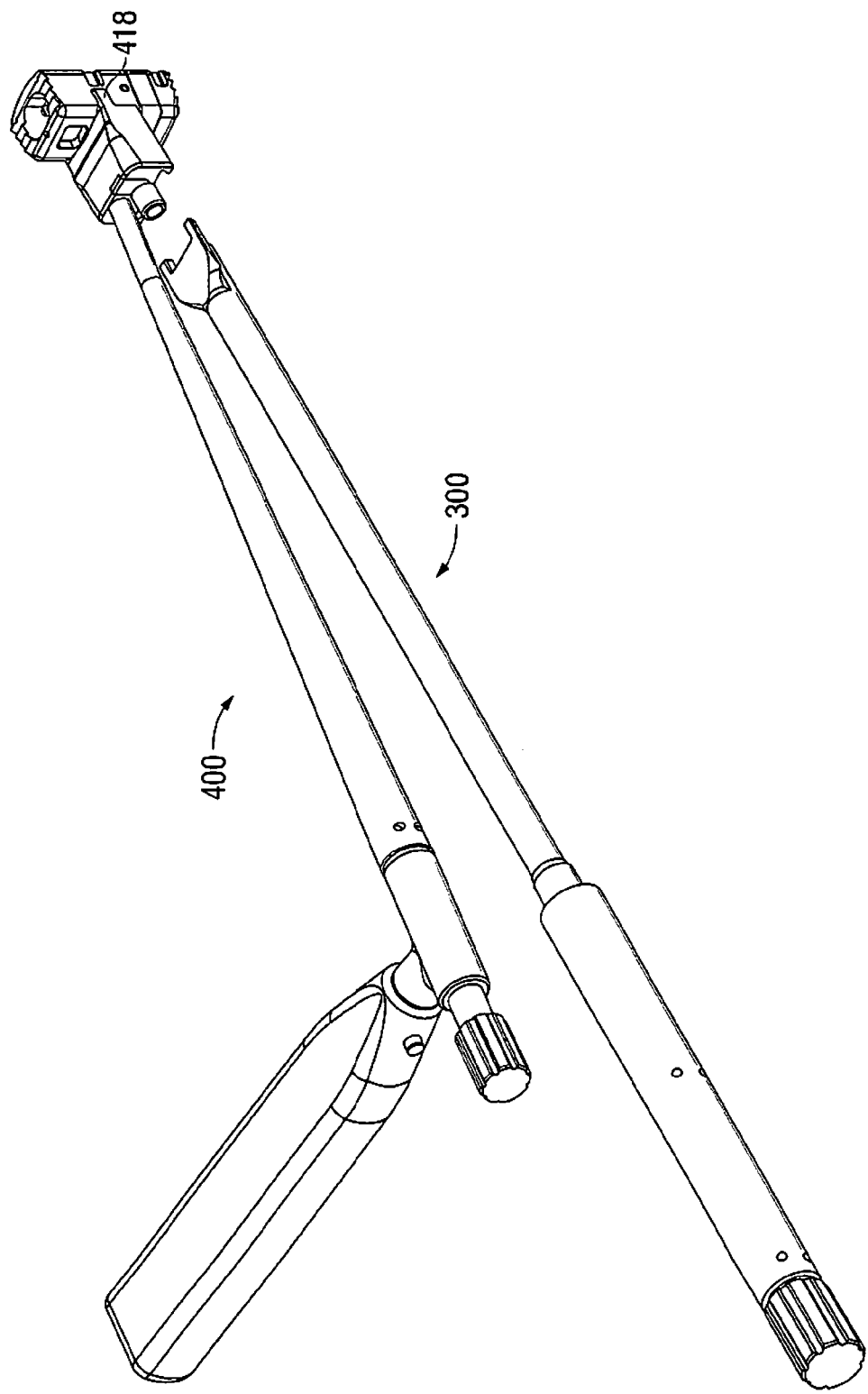
FIG. 51 is a perspective view of the driver of FIG. 24 and the insertion tool of FIG. 36 holding the expandable cage of FIG. 15.

With reference to FIG. 48, bar 444 of holding section 406 includes a plurality of teeth 486 protruding proximally from proximal portion 446. Teeth 486 are disposed annularly on a proximal surface 492 (FIG. 41) of bar 444 and are oriented at an oblique angle with respect to bar 444. Holding section 406 defines a recess 488 dimensioned to fixedly receive a tab 490. Tab 490 includes a plurality of teeth 494 adapted to engage teeth 486 of bar 444. Teeth 494 of tab 490 are disposed annularly on a bottom portion of a distal surface 946 of tab 490 and are oriented at an oblique angle with respect to tab 490. The orientations of teeth 486 and 494 allow bar 444 to rotate in one direction, while inhibiting or precluding rotation of bar 444 in the opposite direction.

Figure 52:
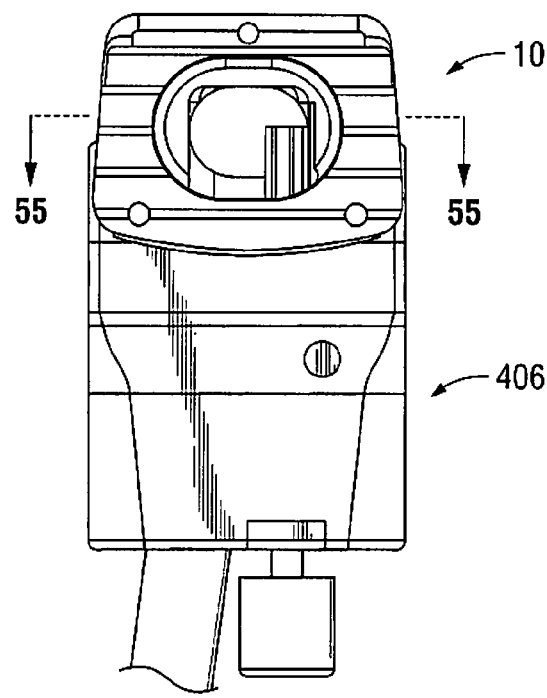
FIG. 52 is a top view of the distal portion of the insertion tool of FIG. 36 holding the expandable cage of FIG. 15.
Figure 53:
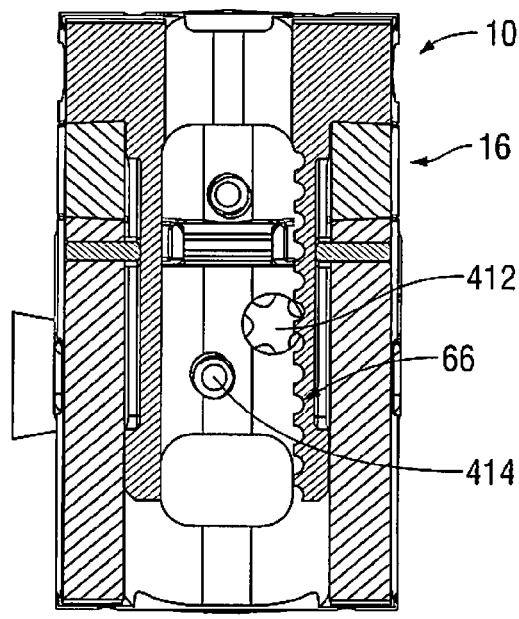
FIG. 53 is a front cross-sectional view of the distal portion of the insertion tool of FIG. 36 holding the expandable cage of FIG. 15, taken along section line 53-53 of FIG. 52.

Referring to FIGS. 49-53, a user can employ driver 300 and insertion tool 400 to place and expand expandable cage 10 in the desired surgical site. First, the user positions holding portion 406 of insertion tool 400 on expandable cage 10 so that first and second arms 416, 418 (FIG. 37) are disposed in cavities 82, 84 (FIGS. 4 and 5). While first and second arms 416, 418 are placed in cavities 82, 84, hexalobular head 412 of insertion tool 400 passes through opening 96 (FIG. 7) of expandable cage 10 to reach rack 66, and threaded tip 414 of insertion tool 400 (FIG. 37) passes through opening 94 (FIG. 7) of expandable cage 10. Whilst inserting threaded tip 414 of insertion tool 400 into opening 94 of expandable cage 10, the user rotates rod 424 via knob 432 to threadably engage thread 422 of threaded tip 414 to thread 95 of opening 94, thereby fixing holding section 406 of insertion tool 400 to expandable cage 10 (FIG. 52).

After securing insertion tool 400 to expandable cage 10, the user advances insertion tool 400 toward the desired surgical site to position expandable cage 10 in a space between vertebrae. Once expandable cage 10 has been positioned between the vertebrae, the user moves first and second supporting members 12, 14 relative to each other to adjust the height of expandable cage 10. In order to displace first and second supporting members 12, 14 relative to each other, the user first positions threaded tip 314 of driver 300 (FIGS. 24 and 25) into socket 452 of insertion tool 400. Next, the user rotates rod 322 of driver 300 through knob 228 to urge the rotation of hexalobular head 412. As hexalobular head 412 rotates while engaging rack 66, first and second supporting members 12, 14 move apart relative to each other to adjust the height of expandable cage 10. The user adjusts the height of expandable cage 10 until a first supporting end 20 and second supporting end 74 engage the vertebral bodies of adjacent vertebrae.

Subsequently, the user detaches driver 300 from insertion tool 400 and holds expansion member 16 with driver 300 as discussed in detail above (See FIGS. 32-35). The user then advances driver 300 toward expandable cage 10 to position expansion member 16 between first and second supporting members 12, 14. As expansion member 16 is placed between first and second supporting members 12, 16, locking portion 60 of expansion member 16 engages locking recesses 58, 64 (FIG. 3) to fix expansion member 16 to expandable cage 10. Once expansion member 16 has been secured to first and second supporting members 12, 16, expansion member 16 maintains the relative position of first and second supporting members 12, 14 of expandable cage 10. Optionally, the user packs the space between adjacent vertebrae with bone support matrix.

It will be understood that various modifications may be made to the embodiments of the presently disclosed expandable cage and insertion tool. Therefore, the above description should not be construed as limiting, but merely as exemplifications of embodiments. Those skilled in the art will envision other modifications within the scope and spirit of the present disclosure.

What is claimed is:

1. An apparatus for spinal surgery, comprising:
   a first supporting member having a first longitudinal passage extending therethrough, and having a first supporting end configured to engage tissue;
   a second supporting member having a second longitudinal passage extending therethrough and a second supporting end, the second longitudinal passage being dimensioned to receive at least a portion of the first supporting member, the second supporting end being configured to engage tissue, wherein the first and second supporting members are configured to move with respect to each other; and
   an expansion member configured for removable placement between the first and second supporting members to maintain the first and second supporting members in a fixed relationship, the expansion member including a backspan, a locking portion disposed on the backspan, and first and second legs extending from the backspan, the locking portion including at least one movable cantilevered arm coupled to the locking portion, the at least one movable cantilevered arm being configured to engage one of the first and second supporting members to releasably secure the expansion member between the first and second supporting members, the at least one movable cantilevered arm being pivotable between a first configuration where the at least one movable cantilevered arm engages the one of the first and second supporting members and a second configuration where the at least one movable cantilevered arm disengages from the one of the first and second supporting members.

2. The apparatus of claim 1, further including first and second movable cantilevered arms, wherein each of the first and second movable cantilevered arms includes a snap-fit detent.

3. The apparatus of claim 2, wherein each of the first and second supporting members includes a locking receiver, each locking receiver being adapted to securely engage the snap-fit detent of the corresponding movable cantilevered arm.

4. The apparatus of claim 1, wherein the first supporting member includes a rack configured to engage a tool.

5. The apparatus of claim 4, further comprising a pin and a slot formed on the first and second supporting members, wherein the slot is adapted to slidably receive the pin to facilitate relative movement of the first and second supporting members.

6. The apparatus of claim 4, wherein the rack is disposed along an inner surface the first supporting member.

7. The apparatus of claim 6, wherein the second supporting member includes an opening providing access to the rack.

8. The apparatus of claim 4, further including a tool assembly including a handle, an elongate section extending from the handle, a holding section operatively coupled to the elongate section and a bar at least partially disposed within the holding section, the bar including a head having a plurality of teeth and being configured to rotate relative to the holding section; the head of the bar being adapted to engage the rack of the first supporting member, wherein the first and second supporting members are configured to move relative to each other upon rotation of the bar when the head is engaged to the rack.

9. The apparatus of claim 8, wherein the tool assembly includes a rod extending through the elongate section, the rod including a threaded tip positioned at a distal end thereof.

10. The apparatus of claim 9, wherein the expansion member includes a threaded bore configured to threadedly engage the threaded tip of the tool assembly.

11. The apparatus of claim 8, wherein the holding section includes first and second arms defining a gap therebetween, the first and second arms extending distally from the holding section.

12. The apparatus of claim 8, wherein the holding section is adapted to engage the second supporting member with the bar in engagement with the rack.

13. The apparatus of claim 1, wherein at least one of the first and second supporting ends includes a plurality of inclined teeth adapted to engage tissue.

14. The apparatus of claim 1, wherein the locking portion includes at least one snap-fit arm adapted to releasably secure the expansion member to at least one of the first and second supporting member.

15. The apparatus of claim 14, wherein the first supporting member includes a first locking recess and the second supporting member includes a second locking recess, the first and second locking recesses being adapted to securely receive the at least one snap-fit arm of the expansion member.

16. The apparatus of claim 15, wherein at least one of the first and second locking recesses includes an engagement wall configured to securely engage the at least one snap-fit arm to couple the expansion member to the first and second supporting members.

17. The apparatus of claim 1, wherein the first supporting member includes a first elongate body extending from first supporting end, the first elongate body defining the first longitudinal passage and the second supporting member includes a second elongate body extending from second supporting end, the second elongate body defining the second longitudinal passage, wherein the second longitudinal passage is configured to receive the first elongate body.

18. The apparatus of claim 17, wherein the first elongate body includes at least one slot defined therealong, the at least one slot being adapted to slidably receive a pin.

19. The apparatus of claim 2, wherein each of the first and second supporting members includes a locking recess configured to securely receive the locking portion of the expansion member.

20. The apparatus of claim 1, wherein the expansion member defines a pre-determined fixed height.

21. The apparatus of claim 1, wherein the first and second legs and the backspan of the expansion member are coplanar.

* * * * *